United States Patent
Huang et al.

(10) Patent No.: US 9,380,938 B2
(45) Date of Patent: Jul. 5, 2016

(54) SYSTEM AND METHODS FOR DOCUMENTING AND RECORDING OF THE PUPILLARY RED REFLEX TEST AND CORNEAL LIGHT REFLEX SCREENING OF THE EYE IN INFANTS AND YOUNG CHILDREN

(75) Inventors: David Huang, Portland, OR (US); Alan Linn Murphree, Pasadena, CA (US); Hiroshi Ishikawa, Allison Park, PA (US)

(73) Assignee: Gobiquity, Inc., Aliso Viejo, CA (US)

( * ) Notice: Subject to any disclaimer, the term of this patent is extended or adjusted under 35 U.S.C. 154(b) by 94 days.

(21) Appl. No.: 13/605,312

(22) Filed: Sep. 6, 2012

(65) Prior Publication Data

US 2013/0235346 A1   Sep. 12, 2013

Related U.S. Application Data

(60) Provisional application No. 61/532,467, filed on Sep. 8, 2011.

(51) Int. Cl.
*A61B 3/15* (2006.01)
*A61B 3/10* (2006.01)
*G06K 9/00* (2006.01)

(52) U.S. Cl.
CPC . *A61B 3/152* (2013.01); *A61B 3/10* (2013.01); *G06K 9/00604* (2013.01); *G06K 9/00912* (2013.01)

(58) Field of Classification Search
CPC .......... A61B 3/14; A61B 3/113; A61B 3/103; A61B 3/1015; G02C 13/005
USPC ......... 351/204, 206, 208, 210, 211, 218, 220, 351/246
See application file for complete search history.

(56) References Cited

U.S. PATENT DOCUMENTS

| 4,989,968 | A | 2/1991 | Freedman |
| 4,995,717 | A | 2/1991 | Damato |

(Continued)

FOREIGN PATENT DOCUMENTS

| EP | 2048615 | 4/2009 |
| KR | 100387356 | 8/2003 |

(Continued)

OTHER PUBLICATIONS

International Search Report, PCT/US2012/053951 filed Sep. 6, 2012. Mailed Feb. 28, 2013.

(Continued)

*Primary Examiner* — Thomas K Pham
*Assistant Examiner* — Jie Lei
(74) *Attorney, Agent, or Firm* — George C. Rondeau, Jr.; Davis Wright Tremaine LLP

(57) ABSTRACT

Systems and methods for documenting, recording, and interpreting the eccentric photorefraction, pupillary light reflex and the corneal light reflex eye screening tests in infants and young children. The system includes a computing device having an image capturing device, a light generating device, and a display. The system includes a computer application that is executable on the computing device and operative to utilize the computing device to perform eye screening tests. The system also includes a website that allows users to upload captured images from the computing device, so that the images may be processed, analyzed, and recorded.

24 Claims, 19 Drawing Sheets

(56) References Cited

U.S. PATENT DOCUMENTS

| | | | |
|---|---|---|---|
| 5,502,520 | A | 3/1996 | Cibis et al. |
| 5,565,949 | A | 10/1996 | Kasha, Jr. |
| 5,886,770 | A | 3/1999 | Damato |
| 5,920,375 | A | 7/1999 | Fahle et al. |
| 5,946,075 | A | 8/1999 | Horn |
| 5,989,194 | A | 11/1999 | Davenport |
| 6,089,715 | A | 7/2000 | Hoover |
| 6,364,486 | B1 | 4/2002 | Ball et al. |
| 6,523,954 | B1 | 2/2003 | Kennedy |
| 6,592,223 | B1 | 7/2003 | Stern et al. |
| 6,616,277 | B1 | 9/2003 | Davenport |
| 6,663,242 | B1 | 12/2003 | Davenport |
| 6,808,267 | B2 | 10/2004 | O'Neil et al. |
| 7,287,857 | B2 | 10/2007 | Glaser |
| 7,665,847 | B2 | 2/2010 | Alster et al. |
| 7,878,652 | B2 | 2/2011 | Chen |
| 7,926,943 | B1 | 4/2011 | Reichow et al. |
| 2003/0020873 | A1 | 1/2003 | Fink et al. |
| 2003/0085996 | A1 | 5/2003 | Horiguchi |
| 2003/0169334 | A1 | 9/2003 | Braithwaite et al. |
| 2005/0270386 | A1 | 12/2005 | Saitoh et al. |
| 2006/0114414 | A1 | 6/2006 | McGrath et al. |
| 2007/0182928 | A1 | 8/2007 | Sabel |
| 2008/0013047 | A1 | 1/2008 | Todd et al. |
| 2008/0058655 | A1 | 3/2008 | Severns |
| 2009/0059169 | A1 | 3/2009 | Shimizu et al. |
| 2009/0079937 | A1 | 3/2009 | Chen et al. |
| 2009/0079939 | A1 | 3/2009 | Mimura |
| 2009/0153799 | A1* | 6/2009 | Johns .......................... 351/206 |
| 2009/0180071 | A1 | 7/2009 | Fateh |
| 2010/0128222 | A1 | 5/2010 | Donaldson |
| 2010/0128223 | A1 | 5/2010 | Blumenthal et al. |
| 2010/0195051 | A1 | 8/2010 | Murray et al. |
| 2011/0085138 | A1 | 4/2011 | Filar |
| 2012/0016763 | A1 | 1/2012 | Kirschner |

FOREIGN PATENT DOCUMENTS

| | | |
|---|---|---|
| WO | 2008005848 | 1/2008 |
| WO | 2010132304 | 11/2010 |
| WO | 2010132304 A1 | 11/2010 |

OTHER PUBLICATIONS

International Search Report mailed Mar. 4, 2013, PCT/US2012/066387 filed Nov. 21, 2012.
American Academy of Pediatrics: Red Reflex Examination in Neonates, Infants, and Children; Pediatrics (Journal); Dec. 2008, vol. 122, No, 6; pp. 1401-4; US.
American Academy of Pediatrics, American Association of Pediatric Ophthalmology and Strabismus, and the American Academy of Ophthalmology; Eye Examination in Infants, Children, and Young Adults Pediatrics (Journal); Apr. 2003; vol. 111, No. 4 ; pp. 902-7; US.
Eventov-Friedman, et al.; The Red Reflex Examination in Neonates: An Efficient Tool for Early Diagnosis of Congenital Ocular Diseases; Imaj (Journal); May 2010; vol. 12; pp. 259-261; Israel.
Roe and Guyton; The Light that Leaks: Bruckner and the Red Reflex; Survey of Ophthalmology; May-Jun. 1984; vol. 28; pp. 665-70; US.
Tongue and Cibis; Brückner Test; Ophthalmology (Journal); 1981; vol. 88, No. 10; pp. 1041-1044; US.
Donahue et al.; Screening for Ambiyogenic Factors Using a Volunteer Lay Network and the MTI PhotoScreener; Ophthalmology (Journal); Sep. 2000; vol. 107, No. 9; pp. 1637-1644; US.
Miller et al.: Comparison of Preschool Vision Screening Methods in a Population with a High Prevalence of Astigmatism; IOVS; Apr. 2001; vol. 42, No. 5; pp. 917-924; US.
Donahue et al.; Sensitivity of Photoscreening to Detect High-Magnitude Ambiyogenic Factors; Journal of AAPOS; Apr. 2002; vol. 6, No. 2; pp. 66-91; US.
Chen et al.; Simulation of Eccentric Photorefraction Images; Optics Express; Mar.-Jun. 2003; vol. 11, No, 14; pp. 1628-1642; US.
Donahue et al.; Preschool Vision Screenings: what Should We be Detecting and How Should We Report It? Uniform Guidelines for Reporting Results of Preschool Vision Screening Studies; Journal of AAPOS; Oct. 2003; vol. 7, No. 5; pp. 314-316; US.
Kovtoun et al; Calibration of Photoscreeners for Single-Subject, Contract-Induced Hyperopic Anisometropia; Journal of Pediatric Ophthalmology & Strabismus; May/Jun. 2004; vol. 41, No. 3; pp. 150-158; US.
Matta et al.; Comparison Between the PlusoptiX and MTI Photoscreeners; Arch Opthalmol; Dec. 2009; vol. 127, No. 12; pp. 1591-1595; US.
Li et al.; The Detection of Simulated Retinoblastoma by Red-Reflex Testing; Pediatrics (Journal); Jul. 2010; vol. 126, No. 1; pp. 201-208; US.
Donahue et al.; US Preventive Services Task Force Vision Screening Recommendations; Pediatrics (Journal); Mar. 2011; vol. 127; No. 3; pp. 568-571; US.
Arnold et al.; Calibration and Validation of 9 Objective Vision Screeners with Contact-Lens Induced Anisometropia; Pediatric Ophthalmology and Strabismus; Mar. 2012; pp. 1-18; US.
Kaakinen, Kari; A Simple Method for Screening of Children with Strabismus, Anisometropia or Ametropia by Simultaneous Photography of the Corneal and the Fundus Reflexes; ACTA Ophthalmologica; Jun. 1978; vol. 57 1979; pp. 161-171; Finland.
Ellis, C.J.K.; The Pupillary Light Reflex in Normal Subjects; British Journal of Ophthalmology; 1981; vol. 65; pp. 754-759; London.
Bobier et al.; Eccentric Photorefraction: Optical Analysis and Empirical Measures; American Journal of Optometry and Physiological Optics; Feb. 1984; vol. 62, No. 9; pp. 614-620; US.
Howland et al.; Optics of Photoretinoscopy: Results from Ray Tracing; American Journal of Optometry and Physiological Optics; Feb. 1985; vol. 62, No. 9; pp. 621-625; US.
Brodie, Scott E.; Photographic Calibration of the Hirschberg Test; Investigative Ophthalmology & Visual Science; Apr. 1987; vol. 28, No. 4; pp. 736-742; US.
Campbell et al; Effect of Monochromatic Aberrations on Photorefractive Patterns; Journal of the Optical Society of America; Aug. 1995; vol. 12, No. 8; pp. 1637-1646; Canada.
Bobier, W.R.; Geometrical Theory to Predict Eccentric Photorefraction Intesity Profiles in the Human Eye; Journal of the Optical Society of America; Aug. 1995; vol. 12, No. 8; pp. 1647-1656; Canada.
Bobier, W.R.; Slope-Based Eccentric Photorefraction: Theoretical Analysis of Different Light Source Configurations and Effects of Ocular Aberatons; Jounal of the Optical Society of America; Oct. 1997; vol. 14, No. 10; pp. 2547-2556; Canada.
Preferential Hyperacuity Perimeter (PHP) Research Group; "Results of a Multicenter Clinical Trial to Evaluate the Preferential Hyperacuity Perimeter for Detection of Age-Related Macular Degeneration," The Journal of Retina and Vitreous Diseases 25:3, 296-303, 2005, Tel-Avia, Israel.
http://www.testvision.org/decide.html, webpage print, 2012.
http://www.visionrx.com/gcheck/Register.asp?frombc=1, webpage print, 2012.
U.S. Appl. No. 13/720,182, filed Dec. 19, 2012, Huang et al.
U.S. Appl. No. 13/683,641, filed Nov. 21, 2012, Huang.

* cited by examiner

SYSTEM AND METHODS FOR DOCUMENTING AND RECORDING OF THE PUPILLARY RED REFLEX TEST AND CORNEAL LIGHT REFLEX SCREENING OF THE EYE IN INFANTS AND YOUNG CHILDREN

CROSS REFERENCE TO RELATED APPLICATIONS

This application claims priority to U.S. Provisional Application No. 61/532,467, filed Sep. 8, 2011, entitled "System and Method for Documenting and Recording of the Pupillary Red Reflex Test and Corneal Light Reflex Screening of the Eye in Infants and Young Children," which is hereby incorporated by reference in its entirety.

BACKGROUND OF THE INVENTION

1. Field of the Invention

The present invention is directed to systems and methods for documenting, recording, and interpreting of the pupillary light reflex and the corneal light reflex eye screening tests in infants and young children.

2. Description of the Related Art

The coaxial ocular fundus reflex (pupillary light reflex test) has been known and taught widely to pediatricians and ophthalmologists as a diagnostic test since the early 1960's. See Roe L D, Guyton D L. The light that leaks: Bruckner and the red reflex. *Surv Ophthalmol* 1984; 28: 665-70, incorporated by reference herein. Light entering the human eye generates a red pupillary light reflex by traveling through the clear ocular media (i.e., the cornea, aqueous humor, lens, and vitreous body) and being reflected back out of the eye. A normal red reflex requires clarity of all ocular focusing elements.

The red pupillary reflex is generated in the following way. Normally, light reaches the transparent retina and is reflected back out of the pupil by the choroid, which is a layer of blood vessels and pigmented cells that nourish the overlying retina. The color imparted to the light reflected back out of the pupil and seen by an observer or instrument that is coaxial to the incident of the entry light is determined by the blood and the amount of pigment in the choroid. Because blood is red and pigment is brown or black, the reflected light will be red (modified by the amount of dark pigment also present). The amount of pigment present in the choroid is correlated with the amount of pigment in the skin. Darker pigmented individuals will normally emit a dark red or red-gray light whereas blonde or lighter pigmented individuals will have bright red or orange-yellow reflected light. The color and intensity of the light from the two pupils in one individual, however, should be symmetrical.

In 1962, Bruckner described abnormalities in the appearance of the quality, intensity, and symmetry of the light reflex from the two eyes as a screening tool. See Tongue A C, Cibis G W. Brückner test. *Ophthalmology*. 1981; 88:1041-1044, incorporated by reference herein. Subsequent authors have recommended the "Bruckner test" for clinically diagnosing misalignment of the eyes (strabismus), different sizes of the eyes (anisometropia), abnormal growths in the eye (tumors), abnormal opacities (cataracts, etc.) in the ocular media, and abnormalities in optic nerve transmission of light (i.e., asymmetrical pupil response).

In a 2010 publication from Israel, 11,500 normal newborn infants were screened with the red reflex test over a two year period. See Eventov-Friedman S, Leiba H, Flidel-Rimon O, Juster-Reicher A, and Shinwell E S. The red reflex examination in neonates: An efficient tool for early diagnosis of congenital ocular diseases. *Is Med Assoc J* 2010; 12:259-261, incorporated by reference herein. These authors detected congenital cataracts with an incidence of 1:2300. Although the sensitivity in this study was only 42%, the false positive was only 7/11,500 or 0.0006%. These authors recommend the use of a direct ophthalmoscopy test using the small hand-held ophthalmoscopes that are present in a wall-charger in most physicians' offices. For this test, the ophthalmoscope is set at 0 lens power, held close to the examiner's eye, and focused on each pupil of the patient individually at about 45 centimeters (cm) from the patient's eye. Both eyes are then viewed in quick succession. The red reflex seen in each eye should be similar. Dark spots in the red reflex, a blunted dull red reflex, lack of a red reflex, or presence of a white reflex are all indications for referral to an ophthalmologist. To maximize pupil dilation, the red reflex test is preferably performed in a darkened room. See The American Academy of Pediatrics, American Association of Pediatric Ophthalmology and Strabismus, and the American Academy of Ophthalmology. Eye examination in infants, children, and young adults by pediatricians. *Pediatrics* 2003; 111; 902-7, and American Academy of Pediatrics. Red reflex examination in neonates, infants, and children. *Pediatrics* 2008; 122; 1401-4, incorporated by reference herein.

The publication of the screening article from Israel discussed above led to the Israeli Pediatric Ophthalmology and Neonatal Societies mandating red reflex screening in Israel in 2010. The American Academy of Pediatrics (AAP), The American Association of Pediatric Ophthalmology and Strabismus (AAPOS), and the American Academy of Ophthalmology (AAO) all endorse the AAP's 2008 guidelines for pediatricians in performing the red reflex examination.

In spite of the practice guidelines published by the AAP, most pediatricians still do not adequately perform and document the red reflex examination, and there is no objective documentation in the medical record that the test was performed on a patient. There are two primary reasons that pediatricians fail to adequately detect the red reflex in infants and children: (1) the young child is often not attending to the pupillary illumination (the test subject must be looking directly at the light source for the testing to be successful), and (2) the pediatrician has only a fraction of a second to assess the pupillary reflex before the pupils constrict in response to the bright light from the ophthalmoscope.

Today, most pediatricians are not detecting treatable ocular pathology in a timely fashion because of the difficulty of red reflex testing with a direct ophthalmoscope. There is a need for overcoming these deficiencies discussed above and other reasons that this test is not being used. As will be appreciated, this invention addresses these deficiencies as well as others.

Another variation in the observation of the pupillary reflex, called eccentric photorefraction, is used to assess refractive error in children. Eccentric photorefraction uses a flash source that is eccentrically positioned relative to the camera aperture (Bobier W R, Braddick O J, Eccentric photorefraction: optical analysis and empirical measures. American Journal of Optometry & Physiological Optics, 1985; 62:614-620). A bright crescent appears in the pupillary reflex when the subject eye has sufficient hyperopia or myopia along the meridian of the flash eccentricity. There are existing instruments for performing eccentric photorefraction but they are not widely used due to their bulk and expense.

Another pediatric screening test is the Hirschberg test, in which corneal reflections of a broad-beam flashlight are used to detect strabismus. The drawback of the test is the lack of photographic documentation and quantitative measurement.

DETAILED DESCRIPTION OF THE INVENTION

Network and Hardware

Figure 1:
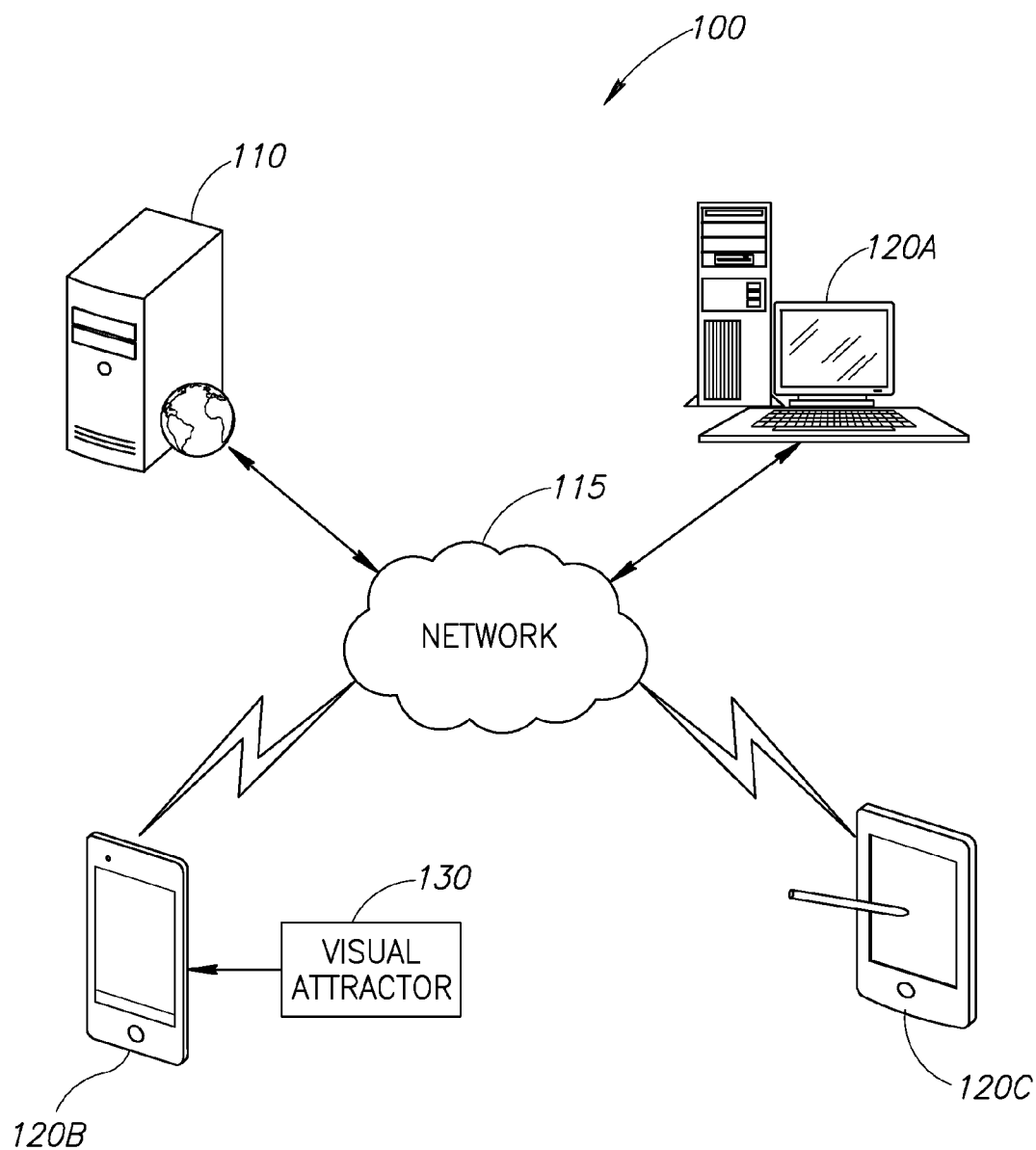
FIG. 1 is a block diagram of a system for documenting, recording, and interpreting of the pupillary light reflex and the corneal light reflex eye screening tests in infants and young children.

The present invention is directed to systems and methods for documenting, recording, and interpreting the pupillary light reflex and the corneal light reflex eye screening tests in infants and young children. FIG. 1 is a simplified illustration of a system 100 that may be used to provide the functionality of the present invention. The system 100 includes at least one server computing device 110 (e.g., a conventional web server or other suitable server), and at least one client computing device (e.g., client computing devices 120A-120C). The server computing device 110 is communicatively connected to the client computing devices 120A-120C by a network 115 (e.g., the Internet, cellular networks, etc.). While the system 100 is illustrated as including the single server computing device 110, those of ordinary skill in the art will appreciate that the system 100 may include any number of server computer devices that each perform the functions of the server computing device 110 or cooperate with one another to perform those functions. Further, while the server computing device 110 is illustrated as being connected to the three client computing devices 120A-120C, those of ordinary skill in the art appreciate that the server computing device may be connected to any number of client computing devices and the server computing device is not limited to use with any particular number of client computing devices.

The client computing devices 120A-120C are each operated by a user, such as a physician, another healthcare provider, a parent, or the like. The client computing devices 120A-120C may each include a conventional web browser configured to display websites, and may be able to execute various types of software applications. By way of non-limiting examples, in FIG. 1, the client computing device 120A is illustrated as a personal computer (e.g., a laptop, personal computer, and the like), the smart phone 120B is illustrated as a smart phone, and the client computing device 120C is illustrated as a tablet computer. Generally, the computing devices 120A-C may include devices that are readily commercially available (e.g., smart phones, tablet computers, etc.), and/or may include devices specifically configured for this particular application. The client computing devices 120A-120C may be located remotely from the server computing device 110.

The client computing devices 120A-120C also each include an image capturing device (e.g., a camera or scanner), a light generating device (e.g., a "flash"), and a computer application or software operative to use the image capturing device and the light generating device to capture images of patients' eyes. It is generally preferred that the light generating device be located close to the lens of the image capturing device.

Each of the client computing devices 120A-120C also includes a screen display that provides a means to frame the patient and to assure focus of the image capturing device. The software of the client computing devices 120A-120C controls the duration and intensity of the light or flash generated by the light generating device.

Referring to FIG. 2, the client computing device 120B is for example a smart phone with camera lens 121 and flash 122 located in close proximity with each other (i.e., separated by a small distance D). The visual attractor 130 is on a back side 16 of the smart phone 120B on the same side as the camera lens 121. By way of non-limiting example, the attractor 130 may be a female face printed on a glow-in-the-dark phone case 129 of the smart phone 120B. This attractor 130 is suitable for attracting the gaze of infant and young children in a dimly lit setting. The smart phone 120B also includes a screen 124 on a front side 160 thereof for real-time display during the photography process.

Figure 2A:
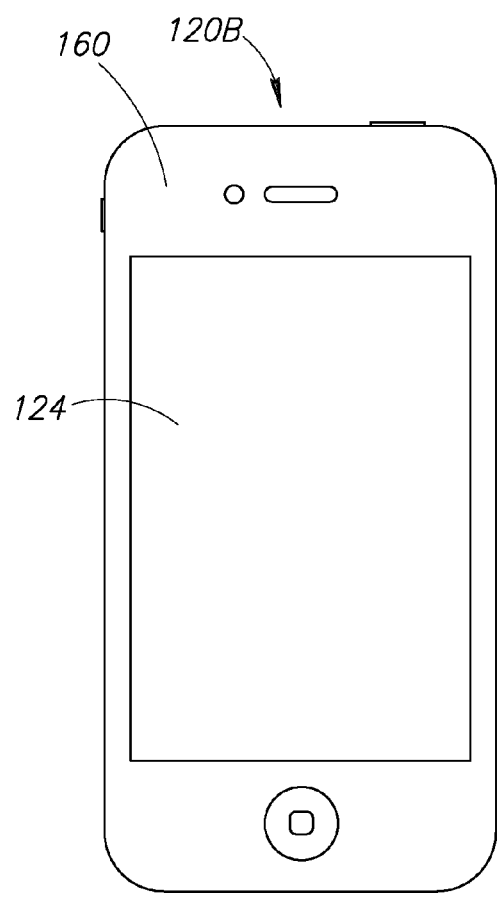
FIG. 2A illustrates a front side of a smart phone in accordance with an embodiment of the present invention.
Figure 2B:
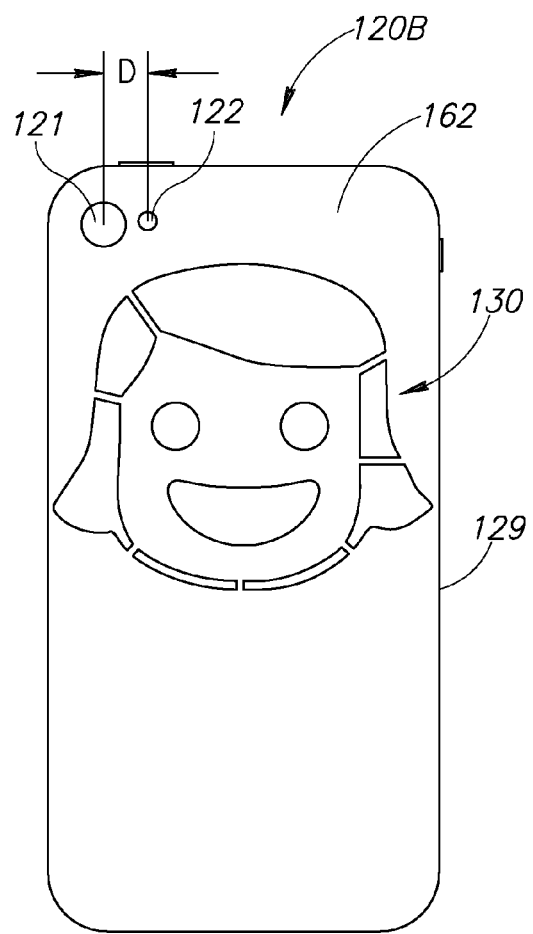
FIG. 2B illustrates a back side of the smart phone showing a camera, flash, and visual attractor.

Referring to FIGS. 2A and 2B, an non-limiting example of the smart phone 120B is the iPhone 4S® sold by Apple, Inc. which has a distance D of approximately 5.7 mm between the camera lens 121 and the flash 122. The flash 122 is located to the right of the lens 121 as shown in FIG. 2B. The particular distance and orientation may be important for the following examples of eccentric photorefraction implemented on the iPhone 4S®. Other smart phones with different flash-camera orientation and distance D may also be used by adjusting the operating distance so the flash-camera distance D subtends a similar visual angle. The orientation the smart phone 120B should be adjusted so the orientation of the flash 122 to the camera lens 121 faces the subject in a similar fashion as to be described below.

Flash Photography Software and Procedures

Figure 3:
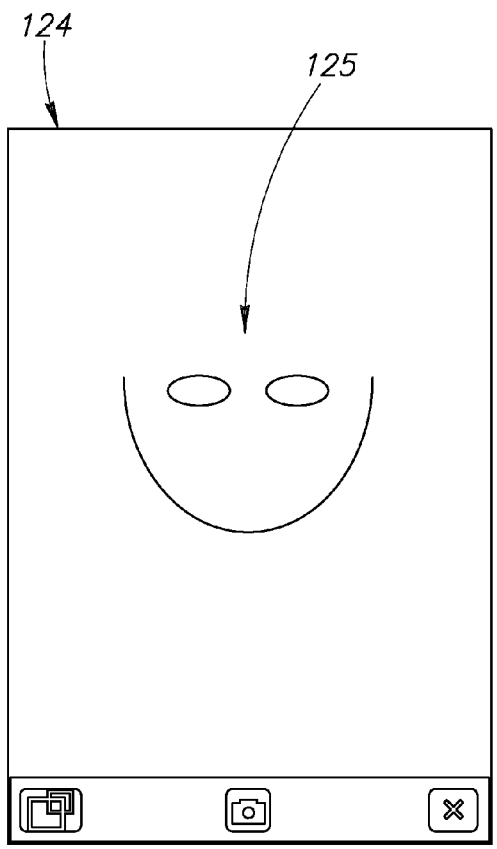
FIG. 3 illustrates a large outline mask shown on a display of the smart phone.
Figure 4:
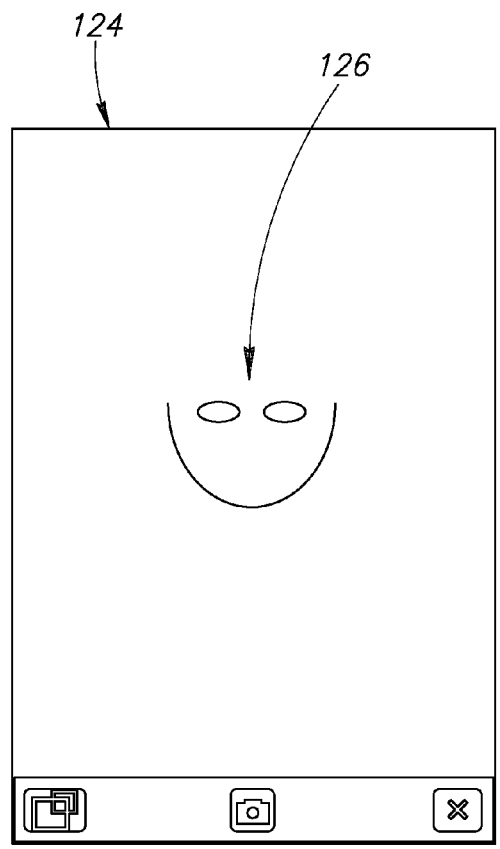
FIG. 4 illustrates a small outline mask shown on a display of the smart phone.

Embodiments of the present invention enable the taking of flash photography of a subject's eyes at set working distances and orientations optimized for eccentric photorefraction, the Bruckner test, and the Hirschberg test—all within the limited capability of computing devices such as the smart phone 120B. According to embodiments of the present invention, the working distance and orientation of photographs are adjusted by the operator (e.g., doctor, technician, or parent) with the aid of outline masks shown on the screen 124 of the smart phone 120B. Referring to FIGS. 3 and 4, the smart phone screen 124 displays an outline mask for the purpose of centration, orientation, and distance adjustment during the photography process. A larger mask 125 (FIG. 3) is used for a closer working distance, and a smaller mask 126 (FIG. 4) is used for a farther working distance.

Embodiments of the present invention include a software program (or "application") executing on the smart phone 120B. The operator activates the application and takes special flash photographs for pediatric photoscreening. Prior to photography, the subject's identifying information (e.g., name, age, birthdate, etc.) may be entered into application.

Figure 5B:
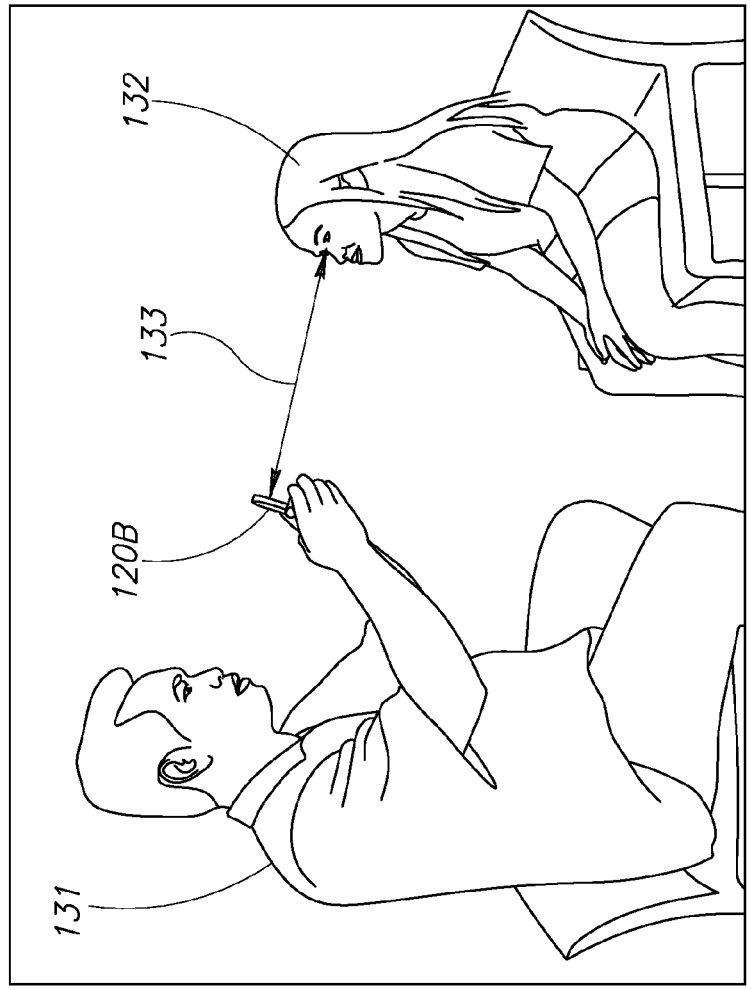
FIG. 5B illustrates the positioning of an operator and a subject during a photography process.
Figure 5A:
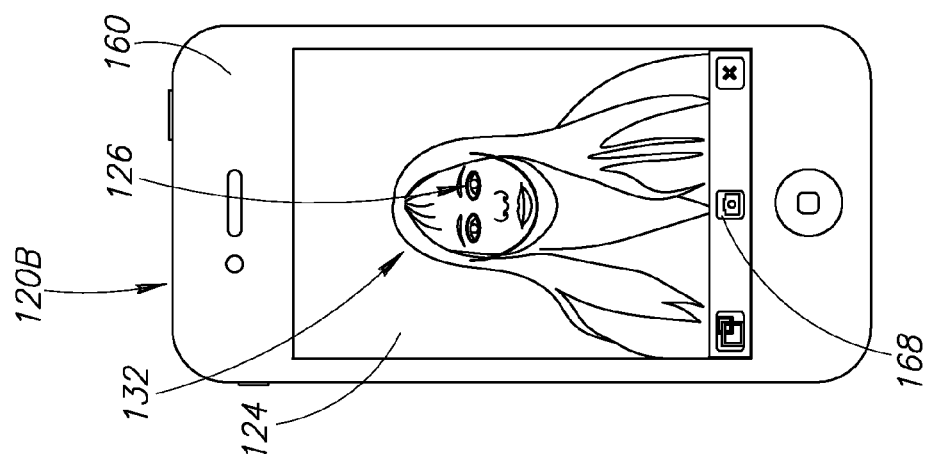
FIG. 5A illustrates the small outline mask aligned with a subject's face during a photography process.
Figure 5C:
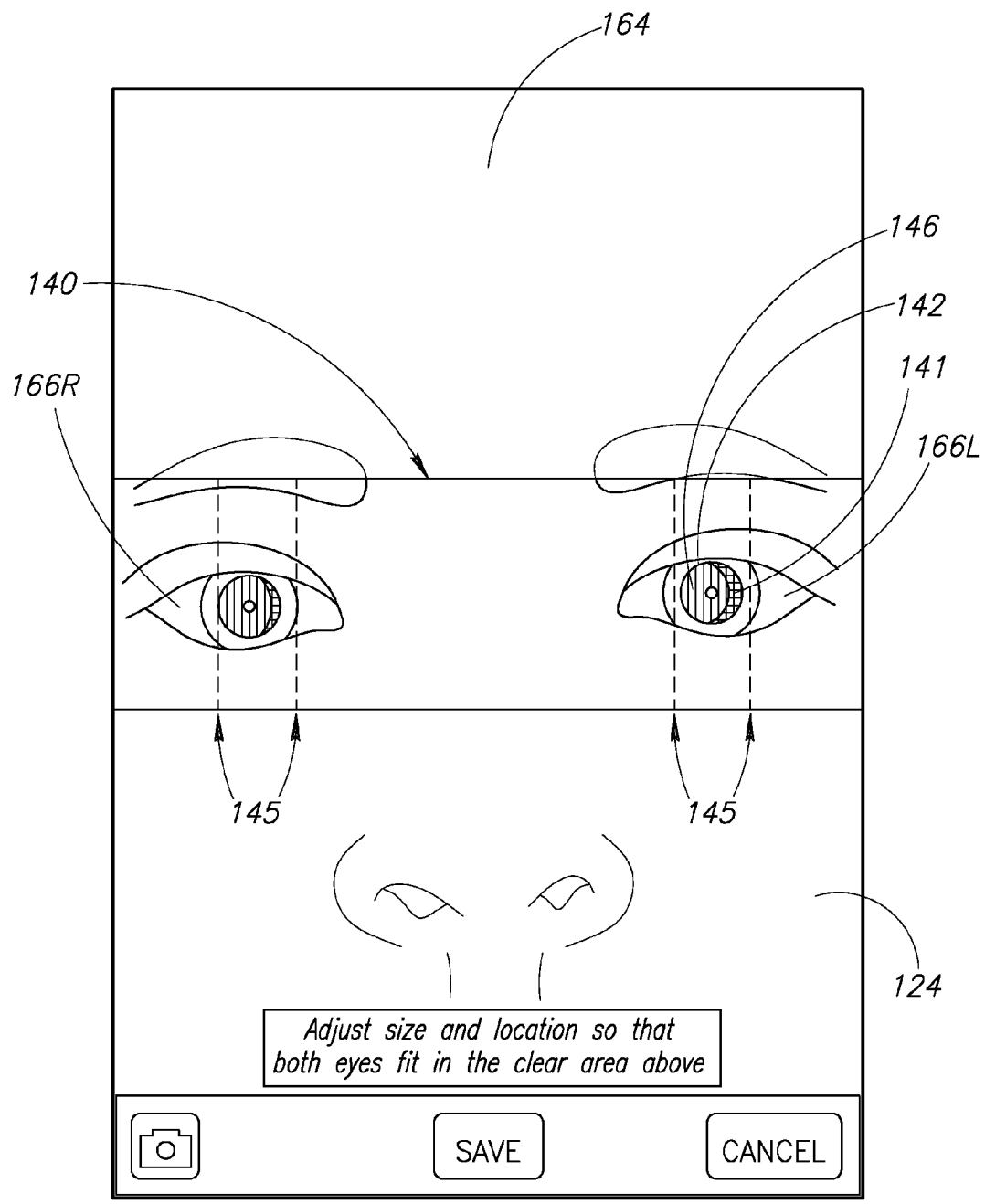
FIG. 5C illustrates a photograph displayed on the display of the smart phone after a photography process.

FIGS. 5A, 5B, and 5C illustrate a process of taking flash photography using the smart phone 120B for the purpose of eccentric photorefraction. It may be helpful for an adult helper to hold infant or very young children to keep them still while the operator takes the photographs. As shown in FIG. 5A, an operator 131 positions the smart phone 120B so as to align the small outline mask 126 to the face of the child subject 132. The outlines of the eyes of the outline mask 126 are carefully matched to the distance between the subject's eyes to establish proper working distance 133 (see FIG. 5B). Once the alignment is found satisfactory, the operator 131 lightly taps a camera button 168 to activate the flash and photographic image capture. Alternatively, other designated buttons could be pressed to activate flash and image capture.

As shown in FIG. 5C, the application then digitally zooms in on the portion of a resulting photograph 164 that contains both eyes 166L, 166R and crops the photograph for immediate display of a zoomed-in photograph in a crop window 140 on the screen 124. The size of the cropped area may be standardized or adjustable. The operator 131 can adjust the position of the cropped area by touching and "dragging" the photograph 164 relative to the crop window 140. The operator 131 adjusts the position of the photograph 164 until the eyes 166L, 166R of the subject 132 are centered in the crop window 140 as shown in FIG. 5C. The centers of both eyes 166L, 166R (as judged by pupils 142 or limbal circles) should fit within the space bracketed between dotted guidelines 145 shown on the display 124. If the working distance 133 is too far or too close so that the inter-eye distance would not allow the eyes 166L, 166R to fit within the displayed guidelines 145, then the photograph 164 should not be saved and another photograph should be taken. Using the guidelines 145, it is ensured that the photograph 164 is within a tolerable range, preferably within approximately +/−15% of the target distance 133.

In a clinical study, the coefficient of variation (CV) of inter-eye distance and corneal diameter were both approximately 5%. In comparison, the CV for working distance 133 was approximately 14% for both the large mask 125 and the small mask 126 (without the use of any guidelines 145 to discard outliers). Thus, using inter-eye distance (or corneal diameter) as a surrogate yardstick to control working distance 133 is a good way to reduce the variability in working distance. In the example shown in FIGS. 5A-5C, the inter-eye distance may be slightly wider than ideal, but well within the range bracketed by guidelines 145. This means the actual working distance 133 may be slightly closer than the ideal distance, but well within acceptable range.

In order to assess photorefraction, a large pupil 142 is needed. Therefore, it is desirable to perform the photography in dim light. Most smart phones (e.g., the smart phone 120B) utilize a pre-flash to constrict the pupil 142 and prevent "red eyes" in the photograph. The program of the current invention deactivates the pre-flash feature of the smart phone 120B. Instead, the flash is timed to coincide with the photographic capture to the pupil diameter. The brightness and duration of the flash is optimized for contrast between the crescent and the red reflex within the pupil.

Referring to FIGS. 5A and 5B, for photorefraction the small mask 126 is used to produce a working distance 133 of approximately 18.5 inches (47 cm). At this working distance, the flash-camera distance D (see FIG. 2B) on the iPhone 4S® subtends approximate 0.7 degrees, which is optimal for the detection of refractive error. Referring to the subject's left eye 166L in this example, the subject 132 is a low hyperope and a bright yellow crescent 141 can be seen on one side of darker red pupillary reflex 146. If the eye 166L had been myopic, the crescent 141 would be on the other side of the pupil 142. According to the principles of eccentric photorefraction, in a hyperopic eye the crescent is seen on the opposite side of the flash 122 relative to the optical axis formed between the camera 121 and eye. In a myopic eye, the crescent is seen on the same side of the flash 122 relative to the optical axis. The degree of refractive error can be estimated from the width of the crescent 141 relative to the pupil 142. This will be described in a later section.

Figure 6A:
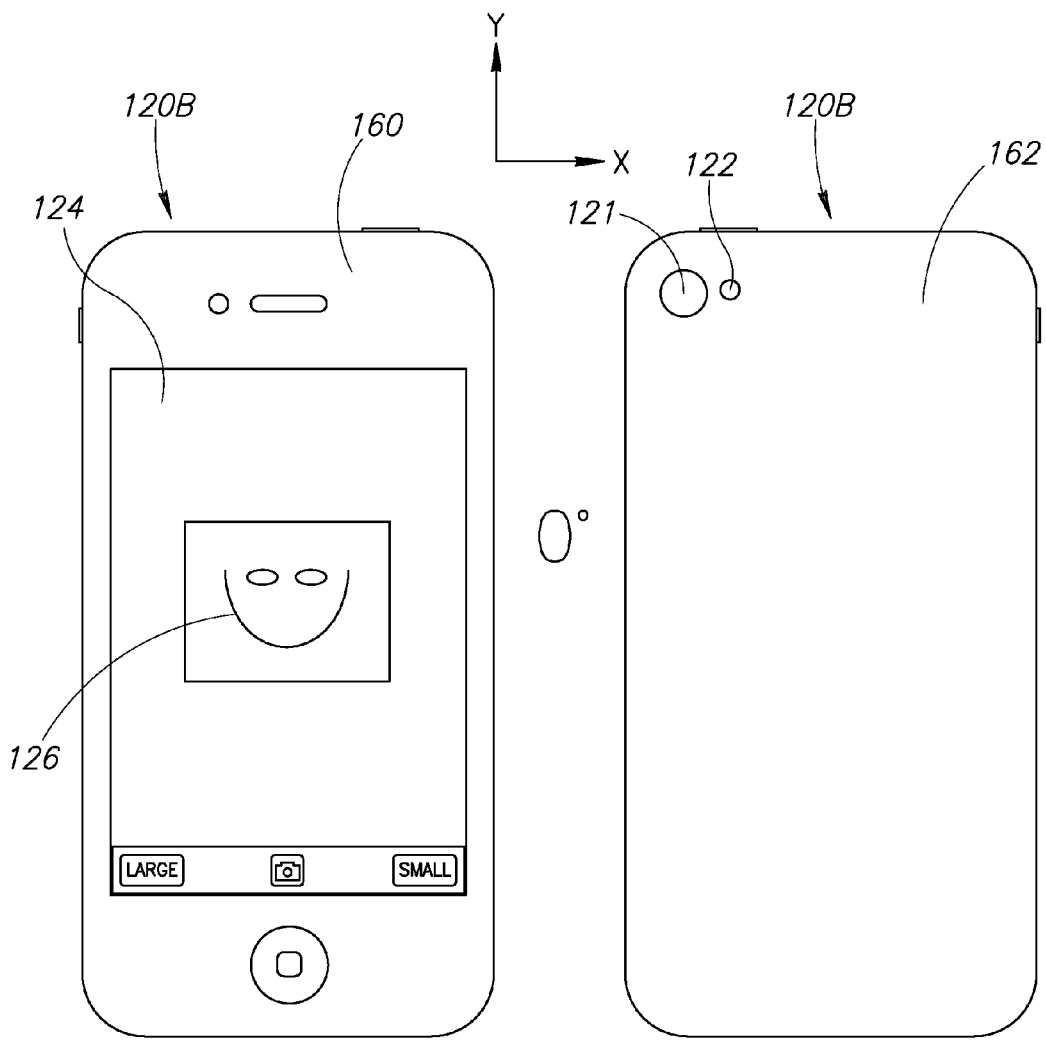
FIG. 6A illustrates a front and back view of the smart phone when oriented at 0 degrees.
Figure 6B:
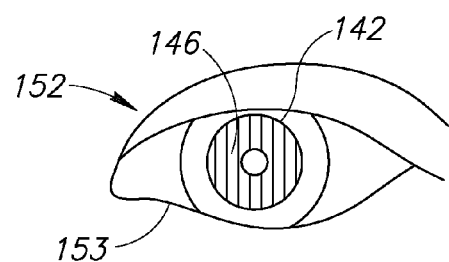
FIG. 6B illustrates an image of a subject's eye taken when the smart phone is oriented at 0 degrees.
Figure 6C:
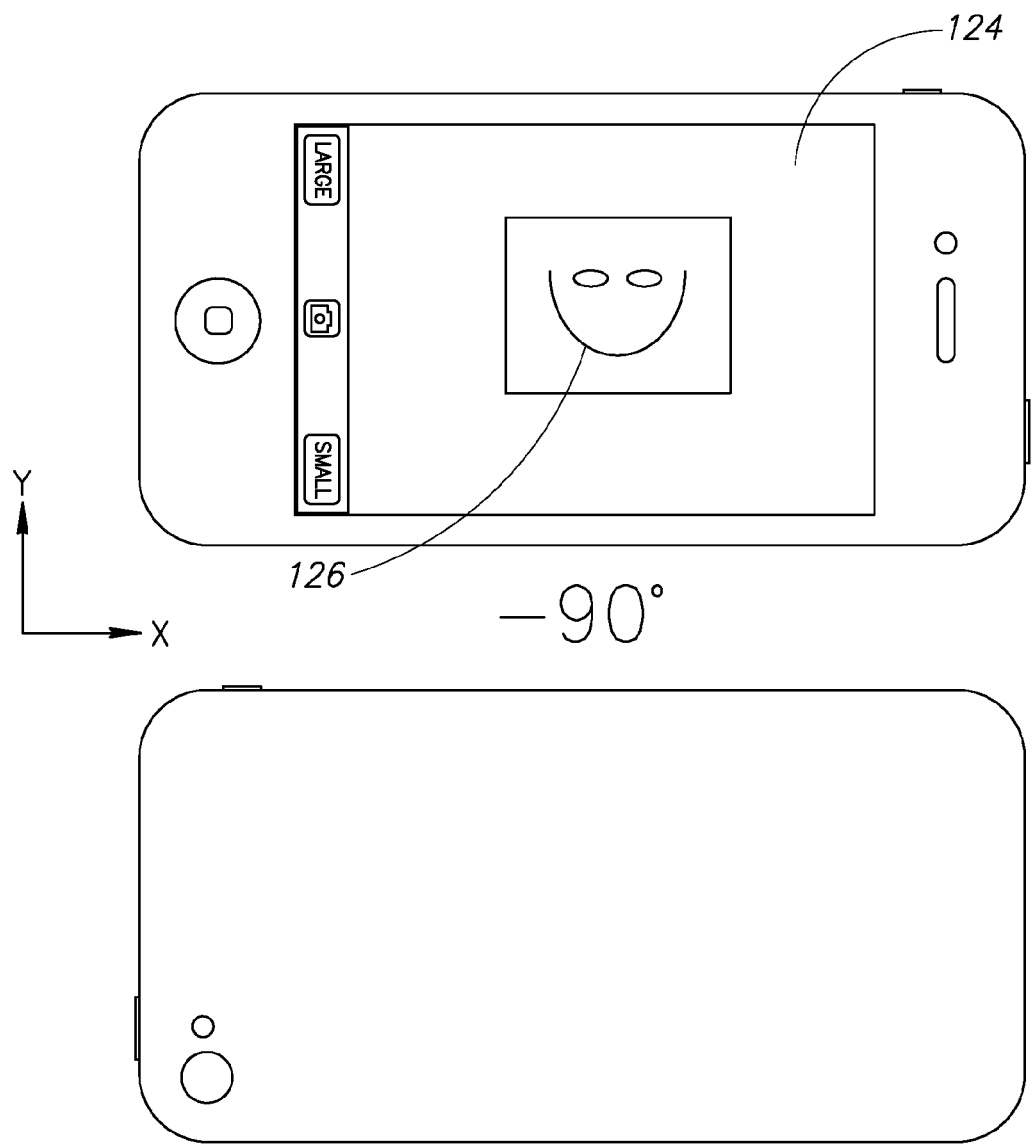
FIG. 6C illustrates a front and back view of the smart phone when oriented at −90 degrees.
Figure 6D:
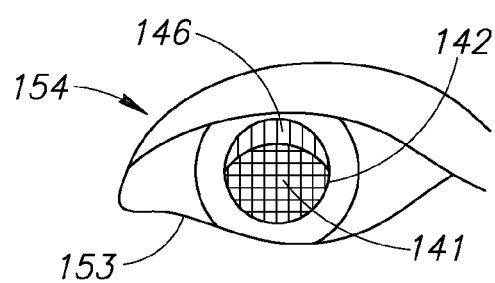
FIG. 6D illustrates an image of a subject's eye taken when the smart phone is oriented at −90 degrees.

In order to detect astigmatism, it is necessary to perform photorefraction in more than one orientation. Referring to FIG. 6A, with the smart phone 120B in upright orientation (0 degrees rotation), the flash 122 is horizontally displaced relative to the camera lens 121, which measures the refraction of the eye along the horizontal meridian. The resulting photograph 152 of FIG. 6B shows an eye 153 to be emmetropia (no refractive error) along the horizontal meridian. To measure the refractive error in the vertical meridian, it is necessary to use sideway orientation, as shown in FIG. 6C. This is accomplished in the present invention by orienting the small mask 126 on the display 124 so that it appears upright when the phone is turned by −90 degrees. In this orientation, the flash 122 is vertically displaced relative to the camera lens 121. This produces a photograph 154 shown in FIG. 6D of the eye 153 that shows high hyperopia along the vertical meridian. The eccentric photorefraction photographs 152 and 154 together show the eye 153 to have a high degree of against-the-rule astigmatism (i.e., the cornea having lower focusing power in the vertical meridian than the horizontal meridian). As an option, it is also possible to orient the outline mask 125 obliquely to assess oblique astigmatism. However, this is generally not necessary for screening purposes as astigmatism is usually oriented close to the horizontal and vertical axes, and is almost never purely oblique in orientation.

Figure 7B:
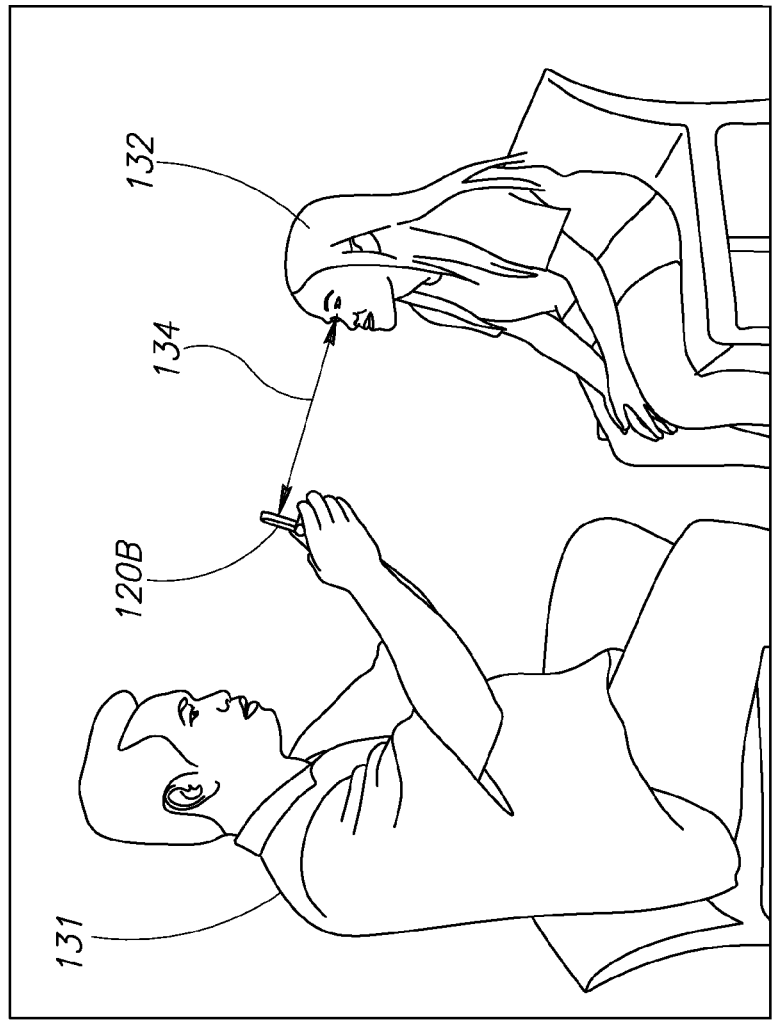
FIG. 7B illustrates the positioning of an operator and a subject during a photography process.
Figure 7A:
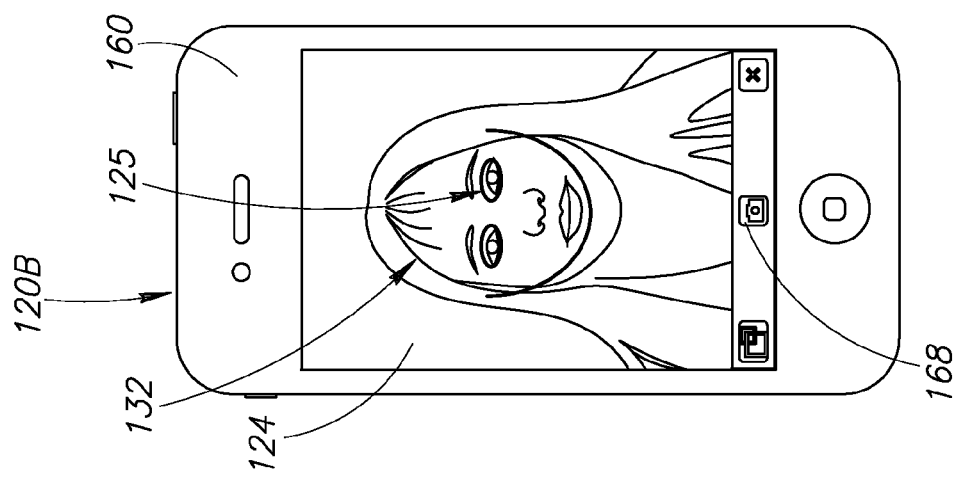
FIG. 7A illustrates the large outline mask aligned with a subject's face during a photography process.
Figure 7C:
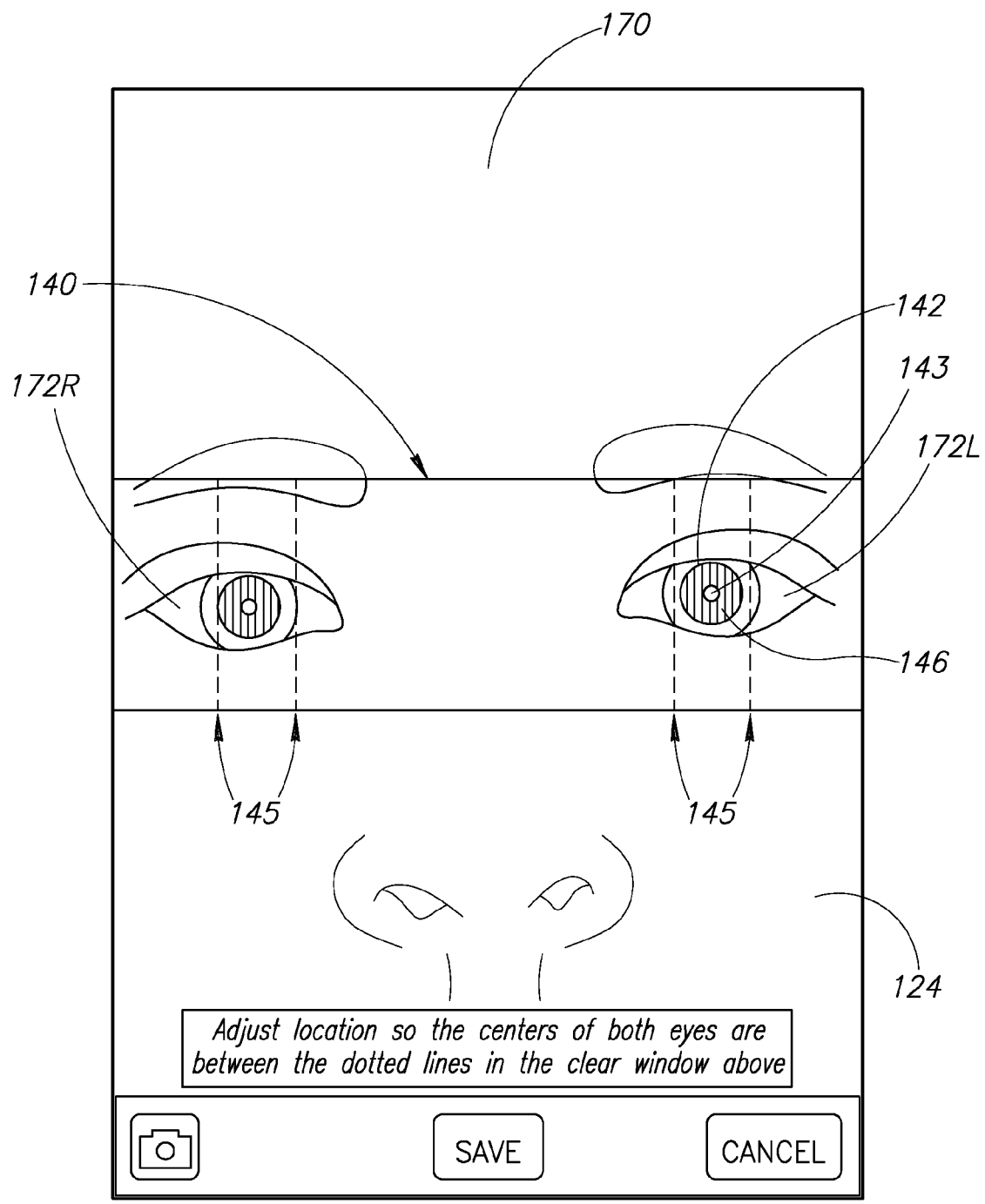
FIG. 7C illustrates a photograph displayed on the display of the smart phone after a photography process.

Because the crescent 141 may obscure the corneal reflex and the pupillary red reflex, it is desirable to minimize the crescent for non-refractive screening purposes. Embodiments of the present invention provide for this by using a closer working distance. Referring to FIGS. 7A, 7B, and 7C, this is accomplished by using the large outline overlay mask 125. For the large mask 125, the working distance 134 may be approximately 12 inches (30 cm). At this working distance 134, the flash-camera distance Don the iPhone 4S® subtends approximate 1.1 degrees, which in most cases (except for extreme myopia or hyperopia) produce no crescent, as shown in the example photograph 170 of FIG. 7C. The pupillary red reflex 146 is seen in full along with a corneal light reflex 143.

A further condition for optimal photography is that external light sources in front of the subject should be avoided, as these extraneous lights could produce additional corneal reflections that interfere with the corneal reflex measurement. The position of the corneal reflex 143 is measured to assess strabismus. The pupillary red reflex 146 is evaluated to detect abnormal shadows or white reflection from media opacity (e.g. cataract) or intraocular tumor (e.g. retinoblastoma). The operator 131 can adjust the position of the cropped area 140 by dragging the photograph 170 relative to the crop window 140. The operator 131 adjusts the position of the photograph 170 until the eyes 172L, 172R are centered in the crop window 140. The centers of both eyes 172L, 172R (as judged by pupils 142 or limbal circles) should fit within the space bracketed between the dotted lines 145. If the working distance 134 is too far or too close so that the inter-eye distance would not allow the eyes to fit within the guidelines 145, then the photograph 170 should not be saved and another photograph should be taken. Using the guidelines 145, the present invention ensures that the photographs are within tolerable range. Since the large mask 125 is used for non-refractive purposes, the tolerance for working distance is wider, preferably within approximately +/−25% of the target distance. In the example in FIGS. 7A, 7B, and 7C, the inter-eye distance is slightly narrower than ideal, but well within the range bracketed by guidelines 145. This means the actual working distance may be slightly farther than the ideal distance, but well within acceptable range.

Figure 8A:
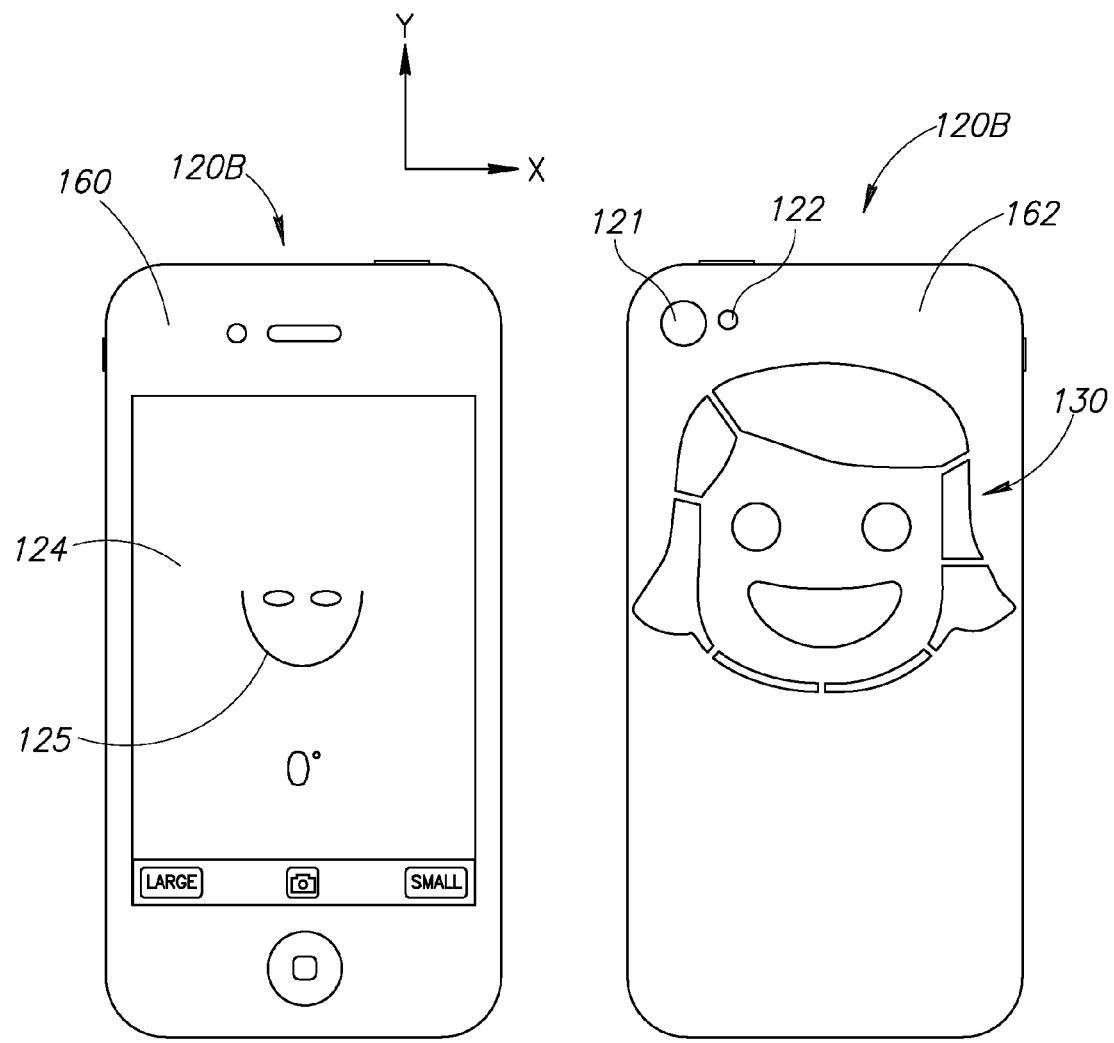
FIG. 8A illustrates a front and back view of the smart phone when oriented at 0 degrees showing the small outline mask displayed upright on the display of the smart phone and the alignment of the camera relative to the flash of the smart phone.
Figure 8B:
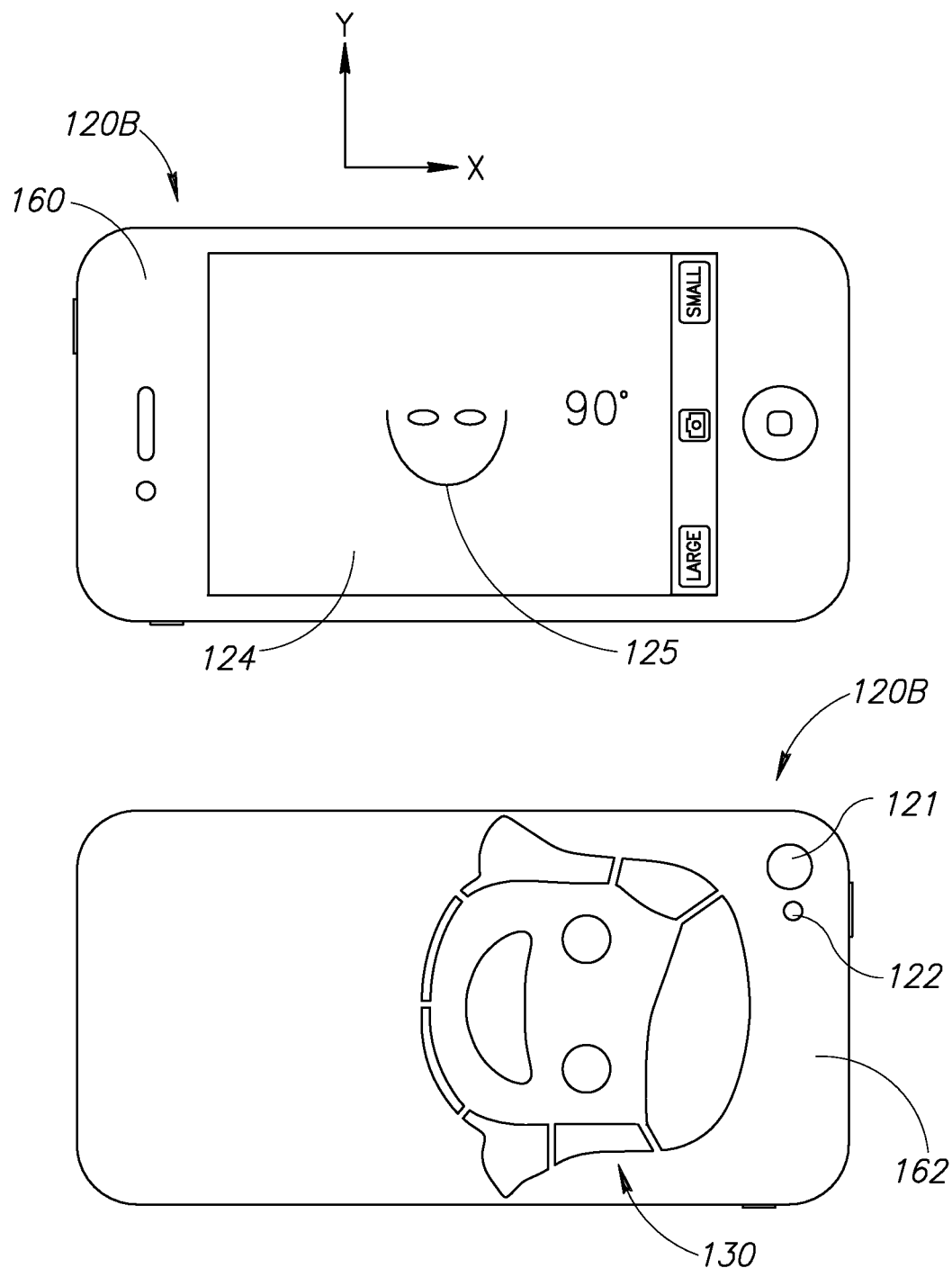
FIG. 8B illustrates a front and back view of the smart phone when oriented at 90 degrees showing the small outline mask displayed upright on the display of the smart phone and the alignment of the camera relative to the flash of the smart phone.
Figure 8C:
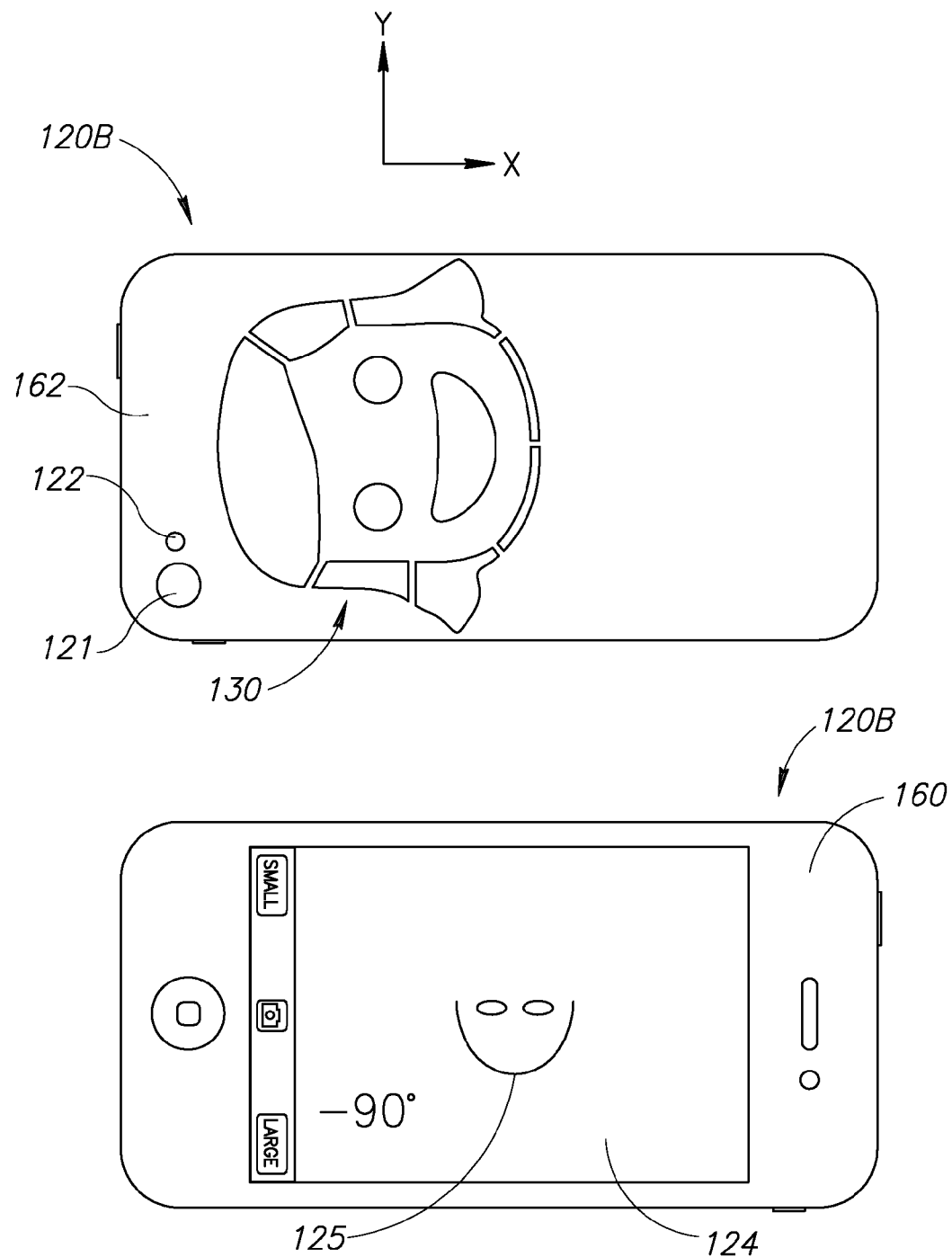
FIG. 8C illustrates a front and back view of the smart phone when oriented at −90 degrees showing the small outline mask displayed upright on the display of the smart phone and the alignment of the camera relative to the flash of the smart phone.
Figure 8D:
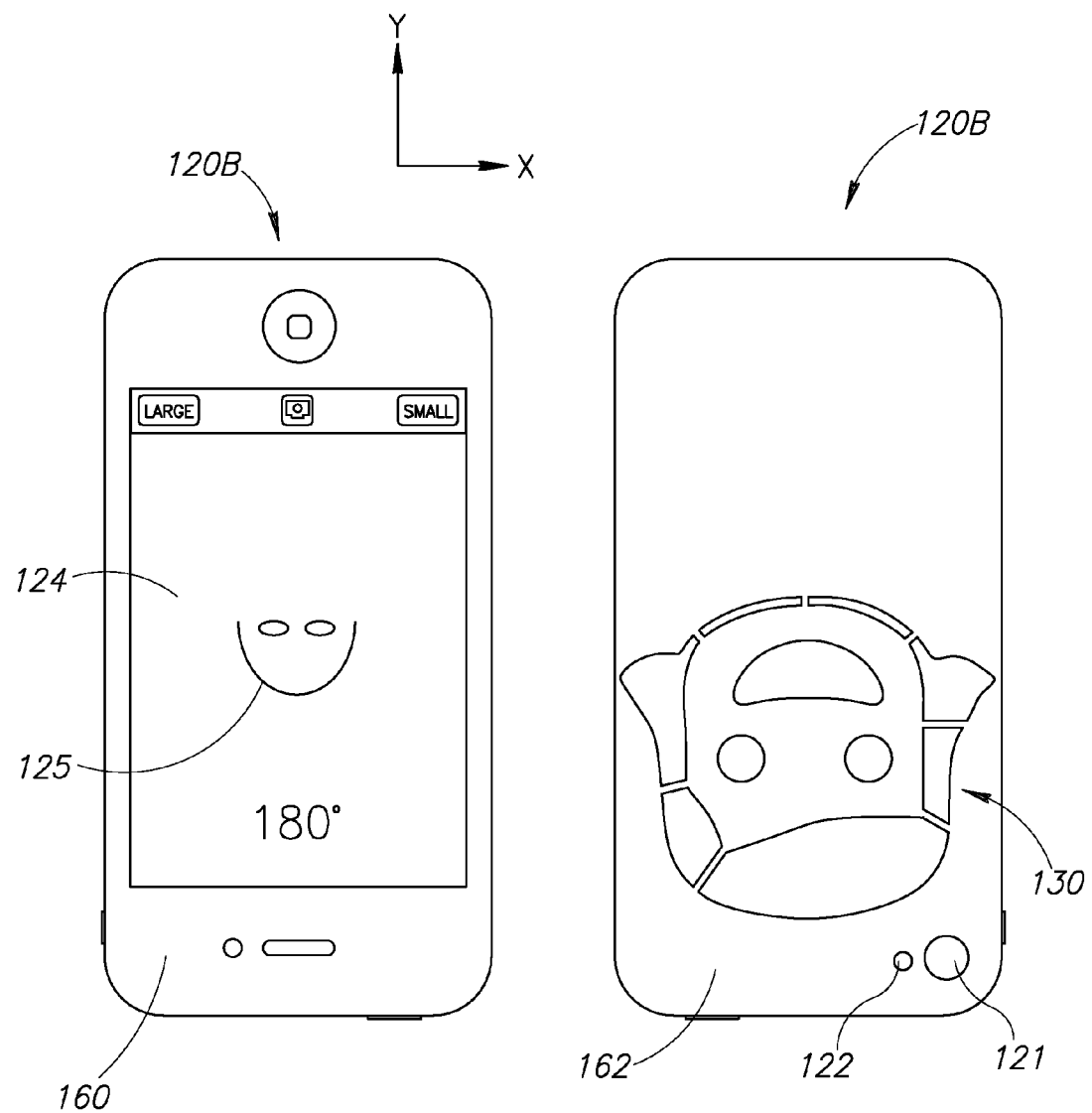
FIG. 8D illustrates a front and back view of the smart phone when oriented at −180 degrees showing the small outline mask displayed upright on the display of the smart phone and the alignment of the camera relative to the flash of the smart phone.

To increase the sensitivity detecting a small retinoblastoma, it is desirable to vary the gaze direction so the flash 122 illuminates different areas on the retina. In the present invention, this is accomplished by varying the orientation of photography. Referring to FIGS. 8A, 8B, 8C, and 8D, the large mask 125 on the display 124 is rotated in four orientations: 0 degrees (FIG. 8A), 90 degrees (FIG. 8B), −90 degrees (FIG. 8C), and 180 degrees (FIG. 8D). A photograph is taken at each orientation. The position of the attractor 130 relative to the flash 122 is different at each orientation. This produces four photographs with different areas of the retina illuminated.

The photoscreening needs of children differ by age. For infants under the age of one year, the primary concerns are cataract, other media opacities, and retinoblastoma. Cataracts and other significant media opacities need to be surgically cleared for eyes to develop vision. Retinoblastoma must be treated early to prevent the tumor from spreading to the brain and become untreatable (i.e., fatal). Refractive errors are of much less concern at this young age. Therefore, according to some embodiments of the present invention, photographs for infants are all done with the large mask 125 and the evaluations are focused on the pupillary red reflex 146 (Bruckner test). The recommended settings for a set of four photographs are listed in Table 1. At least one photograph is needed for an evaluation of the Bruckner test and Hirschberg test. But a complete set of four photographs is preferred for optimal sensitivity of retinoblastoma detection.

TABLE 1

Recommended Photographic Settings for Infants under 1 Year

| Sequence | Mask Size | Phone Orientation |
|---|---|---|
| 1 | L | 0° |
| 2* | L | −90° |
| 3* | L | 180° |
| 4* | L | 90° |

L = large;
*= optional

For children age one year and older, the primary concerns are risk factors for developing amblyopia (lazy eye), which include high refractive error (hyperopia, myopia, astigmatism), unequal refractive error (anisometropia), and strabismus. Therefore, according to embodiments of the present invention, photographs for children are done primarily with the small masks 126. The evaluations include eccentric photorefraction, corneal light reflex (Hirschberg test) and the Bruckner test. If the photorefraction crescents 141 (see FIG. 5C) obscure the corneal light reflexes 143 in the photographs taken with the small mask 126, then the Hirschberg and Bruckner tests cannot be properly carried out. In such cases, two large mask 125 photographs may also be taken. The recommended settings for a set of four photographs are listed in Table 2.

TABLE 2

Recommended Photographic Settings for Children over 1 Year

| Sequence | Mask Size | Phone Orientation |
|---|---|---|
| 1 | S | 0 |
| 2 | S | −90 |
| 3* | L | 0 |
| 4* | L | −90 |

L = large; S = small;
*= Needed if crescent obscures corneal reflex on S.

Photograph Analysis Software and Procedures

Figure 9:
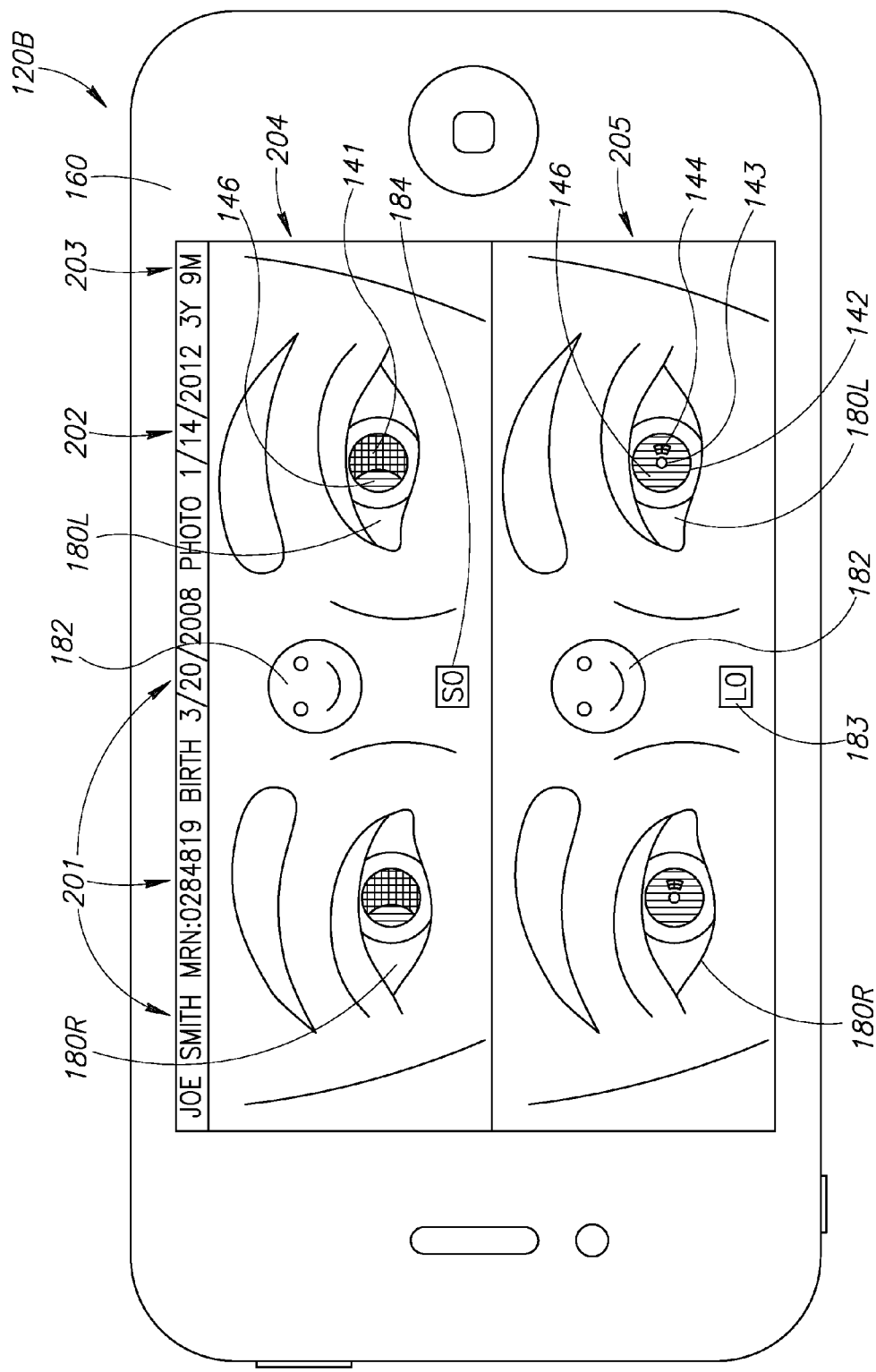
FIG. 9 illustrates two resulting photographs displayed on the display of the smart phone depicting a subject's eyes after a photography screening test.

After flash photographs of the eyes are taken, they are evaluated to screen for eye diseases. The first step according to the present invention is to display these photographs on the display 124 of the smart phone 120B for immediate visual inspection. Referring to FIG. 9, photographs 204 and 205 of the subject's eyes 180L, 180R are displayed in as large a format as possible on the display 124. Since only two photographs fit on the screen 124 in this display format, other photographs taken on the same subject may be rapidly accessible by scrolling (e.g., by finger swiping). Identifying information 201 is provided, along with photography date stamp 202 and the age 203 of the subject. The mask size and orientation information are provided with the photographs 204 and 205 as shown in the boxes 184 and 183 in the photographs 204 and 205, respectively (S0=small mask, 0 degrees; L0=large mask, 0 degrees, etc.). These examples are shown for their instructive nature. The photograph 204 taken with the small mask 126 shows large crescents 141 indicative of high hyperopia, which means this child needs to be referred for full evaluation and treatment by a doctor. The crescents 141 are wider than half of the diameter of the pupils 142 in both eyes 180L, 180R, thus the corneal light reflex 143 cannot be properly visualized in the photograph 204.

This illustrates why another photograph 205 needs to be taken using a large mask 125, as indicated in the box 183 ("L0"). In the photograph 205, the whole reflexes 146 of the pupils 142 are red and the corneal light reflexes 143 from the camera flash can be seen to be well centered in the pupils 142 indicating the eyes are orthotropic (no strabismus). There are secondary reflexes 144 from an extraneous external light source which could interfere with the interpretation of the true corneal reflexes, but fortunately, the secondary reflexes are dimmer, more eccentric, and can be distinguished from the true reflexes 143 and 146. This photograph 205 illustrates the need for the dim room illumination source to be placed to the side behind the plane of the subject's eyes 180L, 180R.

Beyond subjective visual inspection by an expert, the present invention also provides for computer analysis of the eye images. This is preferably performed by automated software on the same smart phone 120B (see FIG. 1) that was used to take the photographs. Alternatively, the photographs can be uploaded through the network 115 to the server computing device 110 where software on the server can perform the automated measurements. The measurements can be verified and adjusted by an expert human (i.e. technician and expert) on a remote client computer 120A.

Figure 10A:
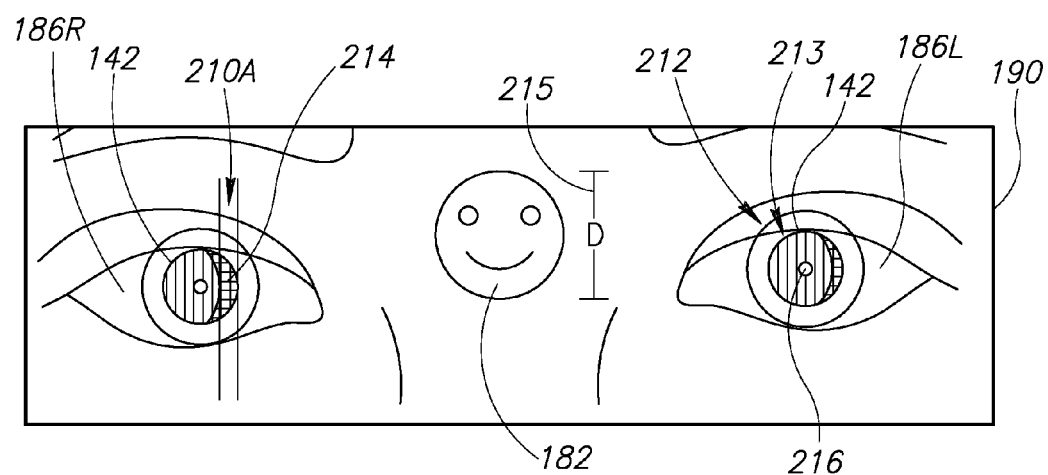
FIG. 10A illustrates a photograph displayed on the display of the smart phone depicting a subject's eyes after a photography screening test.
Figure 10B:
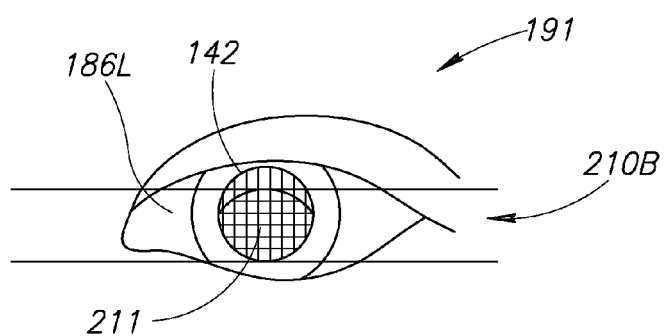
FIG. 10B illustrates a photograph displayed on the display of the smart phone depicting a subject's eyes after a photography screening test.

The computer analyses include measurements of eye dimensions and positions and subsequent computation of diagnostic indices. The measurements below are in units of image pixels, unless otherwise specified. The apparent size in pixel count is then used to compute ratios. Ratios taken over image elements of know size, such as a calibration sticker 182 (see FIG. 9) or corneal diameter, can then be converted to physical dimensions. Referring to FIGS. 10A and 10B, the dimensions of interest include the following:

A photograph 190 is shown depicting a subject's eyes 186L and 186R in FIG. 10A. WH is the width 210A of a horizontal crescent 214, which is positive (hyperopic) if on the left side of the pupil 142 (as shown), and negative (myopic) if on the right side of the pupil. Left and right are defined herein from the subject's perspective, which is opposite of the sidedness on the photograph 190 (i.e. the right eye of the subject is on the left side of the photograph).

FIG. 10B illustrates a photograph 191 of the eye 186L used to measure a vertical crescent 211. WV is the width 210B of the vertical crescent 211, which is positive (hyperopic) if on the bottom of the pupil 142 (as shown), and negative (myopic) if on the top of the pupil. This assumes the photograph is taken with the mask 125 or 126 rotated to the −90 degree position as shown in FIG. 8B.

CD is the corneal diameter measured on limbal circle 212.
PD is the pupillary diameter measured on pupillary circle 213.

SD is the sticker diameter 215 as measured on the sticker 182. In this embodiment, the optional calibration sticker 182 shown has ¾ inch (19.05 mm) diameter and is used to compute working distance and absolute dimensions.

Figure 11:
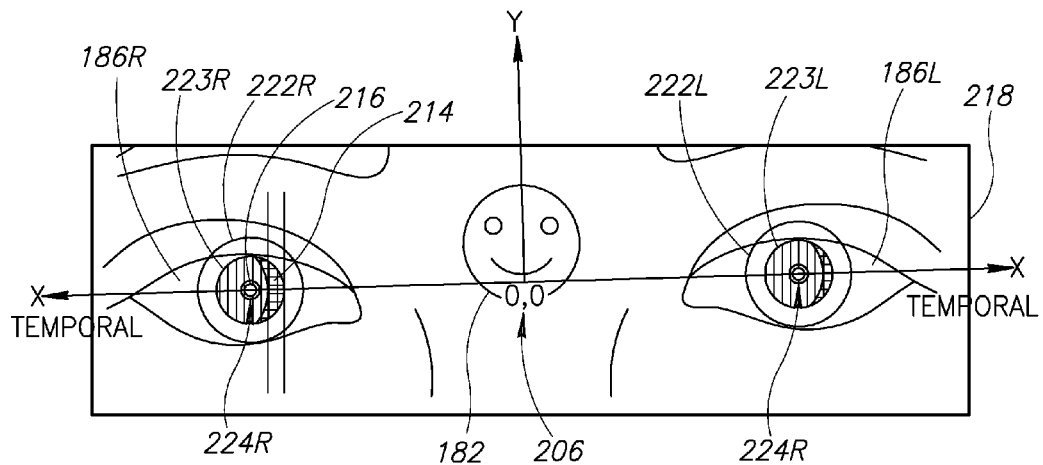
FIG. 11 illustrates a photograph displayed on the display of the smart phone depicting a subject's eyes after a photography screening test.

Referring to FIG. 11, a photograph 218 of the eyes 186L and 186R is shown. The positions of landmarks of the eyes 186L, 186R are measured according to a coordinate system defined by the two limbal circles 222L and 222R. An x-axis connects the centers of the limbal circles 222L and 222R. The x-axis is positive temporally (outward from the nose of the subject). A y-axis is positive upward and negative downward and is oriented perpendicular to the x-axis. An origin 206 of the x-y coordinates is at the midpoint between the limbal circles 222L and 222R. Because the head of the subject is often slightly tilted, the x-y eye coordinates may not be exactly the same as the horizontal and vertical axes of the photograph 218. Thus, position measurements should be transformed from the photograph 218 coordinates to the eye coordinates as shown on FIG. 11. The following positions and dimensions are measured:

ICD is the inter-corneal distance measured between the right limbal circle 222R and left limbal circle 222L.

RXC, RYC are the x and y positions of the cornea as measured at the center of the right limbal circle 222R.

LXC, LYC are the x and y positions of the cornea as measured at the center of the left limbal circle 222L.

RXP, RYP are the x and y positions of the pupil as measured at the center of the right pupillary circle 223R.

LXP, LYP are the x and y positions of the pupil as measured at the center of the left pupillary circle 223L.

RXK, RYK are the x and y positions of the corneal light reflex as measured at the center of the right reflex circle 224R.

LXK, LYK are the x and y positions of the corneal light reflex as measured at the center of the left reflex circle 224L.

The next step after measurements is the computation of diagnostic indices, from which diagnostic classifications can then be made. Diagnostic classifications are based on population references. The following examples and statistics are based on smart phone photographs taken on 65 children in an age range of 3.5 years to 5.3 years (average 4.4 years) who have a range of refractive errors but no strabismus, opacification of ocular media, or intraocular tumor. Following the methods of the present invention, other reference data can also be used. The invention is not limited to the specific threshold values from the example dataset.

Figure 12:
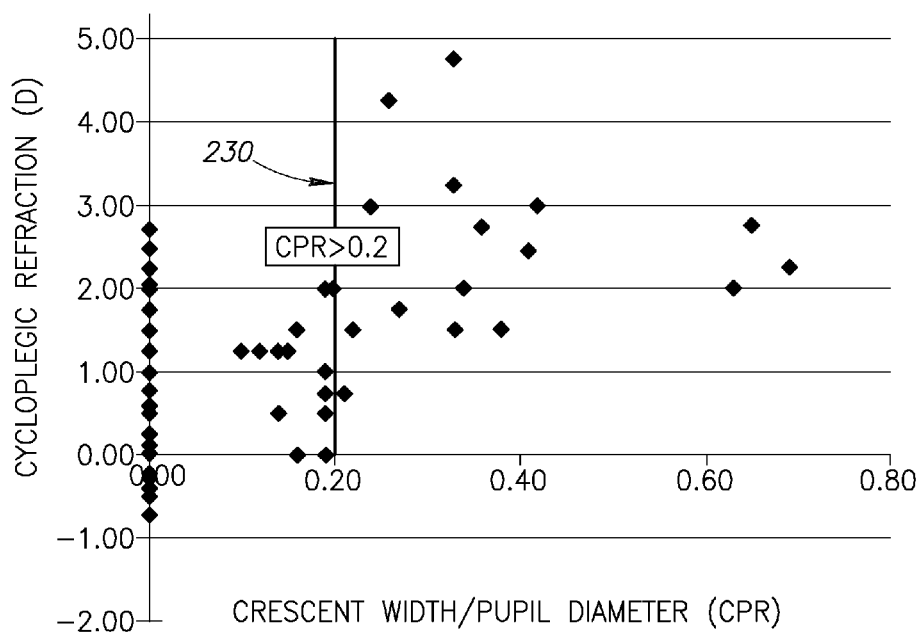
FIG. 12 is a plot of cycloplegic refraction versus crescent width/pupil diameter (CPR) for a plurality of subjects.

According to embodiments of the present invention, eccentric photorefraction is based on the crescent width to pupil diameter ratio (CPR) measured on the photographs taken with the small mask 126. FIG. 12 plots cycloplegic refraction against this ratio for the horizontal meridian. Cycloplegic refraction (CR) is measured with retinoscope by a doctor after the ciliary muscles are paralyzed by the use of cycloplegic eye drops. It is the gold standard for refraction in young children. The photographs, however, were taken prior to the installation of cycloplegic drops. Therefore, the photograph-based eccentric photorefraction could be affected by accommodation (focusing effort) in the measured eye. Referring to FIG. 12, it can be seen that the CPR could be 0 for CR up to 2.8 D. However, by setting a cutoff threshold 230 of CPR>0.2, all cases of CR>3.5 D could be detected. High hyperopia of greater than 3.5 D is the official referral criterion recommended by the American Association of Pediatric Ophthalmology and Strabismus (AAPOS) (Donahue S P, Arnold R W, Ruben J B; AAPOS Vision Screening Committee. Preschool vision screening: what should we be detecting and how should we report it? Uniform guidelines for reporting results of preschool vision screening studies. *J AAPOS*. 2003; 7(5):314-

316). Using CPR>0.2 as the photoscreening criterion, visual inspection of photographs yielded sensitivity of 100% (2/2) for detecting high hyperopia, with a specificity of 90%. Using a CPR difference between left and right eyes of greater than 0.2 as the cutoff, visual inspection yielded a sensitivity of 100% for detecting anisometropia (defined by AAPOS as CR difference of greater than 1.5 D between the two eyes), with a specificity of 95%.

Figure 13:
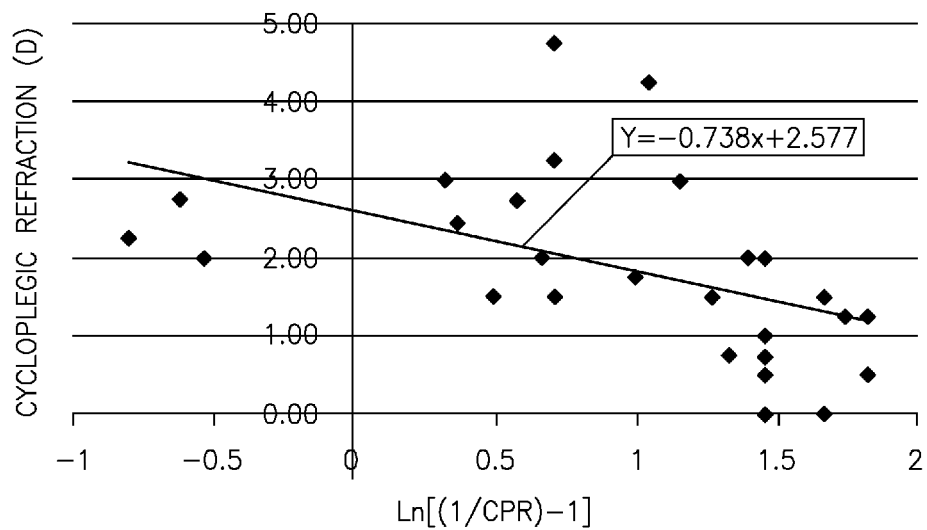
FIG. 13 is a plot of cycloplegic refraction as it is related to photorefraction by a logit function.

It is also desirable to obtain a quantitative estimate of refraction from the photographs. The relationship between refraction and CPR is a sigmoidal one. The crescent is not present between CR of between −2.1 D (corresponding to the working distance of 47 cm with the small mask 126) and a low degree of hyperopia. With greater degrees of hyperopia, CPR increases, but saturates at a value of 1 (i.e., the crescent cannot be wider than the pupil). Therefore, a sigmoidal mathematical function is needed for the fit. The present invention uses the logit function:

$$PR = A * \ln[(1/CPR) - 1] + B \text{ for } CPR > 0$$

where
PR is the photorefraction,
A and B are slope and intercepts from fitting of data (FIG. 13), and
ln [ ] is the natural logarithm function.
A separate curve fit is needed for myopia:

$$PR = F * \ln[(1/CPR) + 1] + G \text{ for } CPR < 0$$

where F and G are slope and intercepts from fitting of data.
For CPR=0 (i.e., no crescent), the refraction can be estimated based on the CPR in the other eye. If the other eye has a positive CPR, then PR can be set to +0.1 D based on empirical data. If the other eye has a negative CPR, the PR is set to −2.1 D. If both eyes have no crescent, then it is safe to assume that both eyes are emmetropic or have insignificant amount of myopia that do not require referral.

Cardinal astigmatism is evaluated by subtracting the PR for the horizontal and vertical meridians:

$$PAst = PRV - PRH$$

where
PAst is the photo cardinal astigmatism (positive for with-the-rule astigmatism and negative for against-the-rule astigmatism),
PRV is the photorefraction in the vertical meridian calculated from the CPR from the photograph taken in −90° orientation, and
PRH is the photorefraction in the horizontal meridian calculated from the CPR from the photograph taken in 0° orientation.

Anisometropia (difference in refraction between two eyes) can be estimated in the horizontal and vertical meridians separately:

$$PAnisomH = Abs(RPRH - LPRH)$$

where
PAnisomH is the photo-anisometropia in the horizontal meridian,
Abs( ) is the absolute value function,
RPRH is the right eye's photorefraction in the horizontal meridian, and
LPRH is the left eye's photorefraction in the horizontal meridian.
Similarly, $$PAnisomV = Abs(RPRV - LPRV)$$

where
PAnisomV is the photo-anisometropia in the vertical meridian,
Abs( ) is the absolute value function,
RPRV is the right eye's photorefraction in the vertical meridian, and
LPRV is the left eye's photorefraction in the vertical meridian.

Table 3 is a summary report of the eccentric photorefraction results based on the two small mask photographs (Table 2) taken at 0° and −90° orientations.

TABLE 3

Photorefraction Summary Report

| Parameter | Right Eye | | | Left Eye | | | Anisometropia | |
|---|---|---|---|---|---|---|---|---|
| | RH | RV | Ast | RH | RV | Ast | AnisomH | AnisomV |
| Estimate Criterion | >1.75D or <−3.0D | >1.5D | | >1.75D or <−3.0D | >1.5D | | >1.5D | | where RH,RV=refractions on horizontal and vertical meridians, respectively; Ast=cardinal astigmatism, and AnisomH, AnisomV=anisometropia on horizontal and vertical meridians, respectively. Estimates are parameter values estimated from the set of two photographs taken at 0° and −90° orientations. Criterion, based on AAPOS criteria with empirical adjustment, is the cutoff beyond which referral to an eye doctor is needed.

Figure 14:
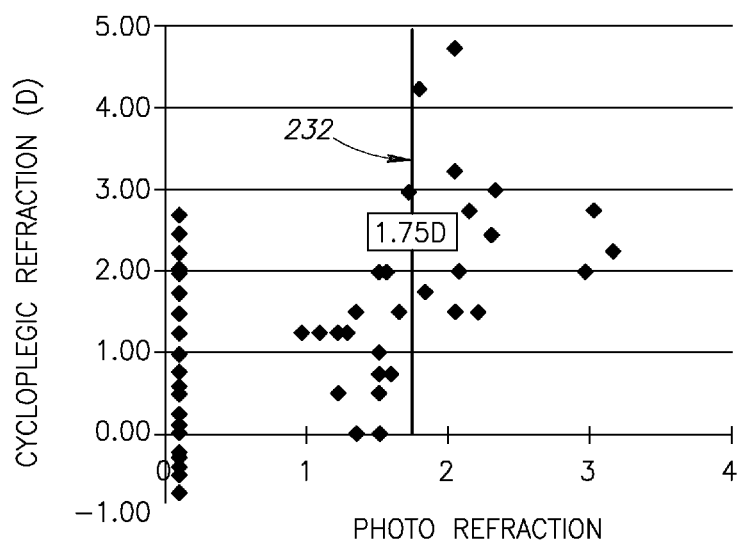
FIG. 14 is a plot of cycloplegic refraction versus photorefraction.

The criterion for hyperopia referral is based on clinical data (see FIG. 14) that shows referring all eyes with photorefraction >1.75 D would catch all eyes with CR>3.5 D. This is a non-limiting exemplary referral criterion. The referral criterion may be customized for different ages and may be revised when new clinical data or official recommendations become available The anisometropia referral criterion of >1.5 D provides for 100% sensitivity (3/3) and 95% specificity in the clinical study. The gold standard used is a difference in CR of >1.5 D according to AAPOS recommendation.

Another aspect of the present invention relates to the measurement of strabismus using a photographic version of the Hirschberg corneal reflex test. In the traditional Hirschberg test, the position of the corneal light reflex is subjectively evaluated by the examiner using a penlight. In a photographic version, it has been found that each millimeter (mm) of deviation of the corneal reflex from its normal position is associated with approximately 21 prism diopters of strabismus (Brodie S E, Photographic calibration of the Hirschberg test, *Invest Ophthalmol Vis Sci* 1987; 28:736-42), the normal position of the corneal reflex being approximately 0.5 mm nasal to the pupillary axis. In the present invention, the position of the corneal reflex is compared to both the pupil circle 213 and the limbal circle 212 (see FIG. 10A). According to the present invention, position offsets are converted to dioptric scales using the corneal diameter 215 as the size reference. Alternatively, the calibration sticker 182 (see FIG. 10A) or the inter-corneal distance could also be used as the size reference. These measurements are preferably made on photographs taken with the large mask 125. However, the small mask 126 could also be used if the crescents are small enough not to interfere with the visualization of the corneal reflex. The following exemplary results were obtained from photographs taken with the large mask 125, unless otherwise specified.

According to the present invention, the following strabismus indices, based on the offset between the pupillary reflex and corneal reflex positions, are calculated.

$$HRGP=A*(RXP-RXK)/RCD$$

$$HLGP=A*(LXP-LXK)/LCD$$

$$VRGP=A*(RYP-RYK)/RCD$$

$$VLGP=A*(LYP-LYK)/LCD$$

$$HSIP=HRGP+HLGP+BP$$

$$VSIP=VRGP-VLGP$$

where

HRGP is the horizontal right eye gaze deviation (prism diopter),

HLGP is the horizontal left eye gaze deviation (prism diopter),

VRGP is the vertical right eye gaze deviation (prism diopter),

VLGP is the vertical left eye gaze deviation (prism diopter),

HSIP is the horizontal strabismus index (prism diopters),

VSIP is the vertical strabismus index based on pupil offset, and

A is a conversion factor and BP is an offset.

HSIP is positive for exotropia and negative for esotropia. VSIP is positive for right hypertropia or left hypotropia, and negative for left hypertropia or right hypotropia. The conversion factor A is 240 prism diopters per corneal diameter calculated by multiplying 21 mm per prism diopter with the average corneal diameter of 11.44 mm from the clinical study. The offset factor BP is −10.7 prism diopters for the large mask 125 and −16.3 prism diopters for the small mask 126, as obtained from the clinical study. When HSIP is outside of normal range, then horizontal strabismus is suspected. When horizontal strabismus is suspected, the fixating eye can be determine by comparing HRGP and HLGP; if HRGP<HLGP then the right eye is fixating (left eye is deviating), otherwise the left eye is fixating. When VSIP is outside of normal range, then vertical strabismus is suspected. When vertical strabismus is suspected, the fixating eye can be determine by comparing VRGP and VLGP; if VRGP<VLGP then the right eye is fixating, otherwise the left eye is fixating.

According to the present invention, the following strabismus indices, based on the offset between the limbal circle and corneal reflex positions, are also calculated.

$$HRGL=A*(RXL-RXK)/RCD$$

$$HLGL=A*(LXL-LXK)/LCD$$

$$VRGL=A*(RYL-RYK)/RCD$$

$$VLGL=A*(LYL-LYK)/LCD$$

$$HSIL=HRGL+HLGL+B$$

$$VSIL=VRGL-VLGL$$

where

HRGL is the horizontal right eye gaze deviation (prism diopter),

HLGL is the horizontal left eye gaze deviation (prism diopter),

VRGL is the vertical right eye gaze deviation (prism diopter),

VLGL is the vertical left eye gaze deviation (prism diopter),

HSIL is the horizontal strabismus index (prism diopters),

VSIL is the vertical strabismus index based on pupil offset, and

A is a conversion factor and BL is an offset.

HSIL is positive for exotropia and negative for esotropia. VSIL is positive for right hypertropia or left hypotropia, and negative for left hypertropia or right hypotropia. The conversion factor A is 240 prism diopters per corneal diameter calculated by multiplying 21 mm per prism diopter with the average corneal diameter of 11.44 mm from the clinical study. The offset factor BL is −23.1 prism diopters for the large mask 125 and −24.8 prism diopters for the small mask 126, as obtained from the clinical study.

The following strabismus summary report (Table 4) provides information for the detection of strabismus. Non-limiting exemplary confidence intervals are based on the mean and standard deviations (SD) values in the clinical study. An assumption of normal distribution was made. Thus, 95% confidence interval (CI) is set by mean+/−1.96 SD and 99% CI is set by mean+/−2.58 SD. For photographs taken with the large mask 125, HSIL has 95% CI of −12.8 to 12.8 prism diopters, and 99% CI of −16.8 to 16.8 prism diopters. HSIP has 95% CI of −12.3 to 12.3 prism diopters, and 99% CI of −16.1 to 16.1 prism diopters. In the summary reports below, values outside 99% CI are preferably highlighted in red to signify "outside normal limits." Values outside 95% CI but within 99% CI are preferably highlighted in yellow to signify "borderline" conditions.

TABLE 4

Strabismus Summary Report

| Offset relative to corneal reflex | Axis | Right Eye | Left Eye | Strabismus Index |
|---|---|---|---|---|
| Pupil | Horizontal | HRGP | HLGP | HSIP |
|  | Vertical | VRGP | VLGP | VSIP |
| Limbal Circle | Horizontal | HRGL | HLGL | HSIL |
|  | Vertical | VRGL | VLGL | VSIL |

When the gaze angle of either of the left or right eyes are sufficiently deviated from the center, the flash illumination could fall on the optic disc and produce an abnormal (white) pupillary reflex. The center of the optic disc (blind spot) is 12 to 15 degrees nasal to the fovea (fixation). The width of the optic disc is approximately 5.5 degrees of visual angle. Therefore, photographs showing gaze angle of more than 9 degrees (16 prism diopters) should not be used. Thus, when any of the horizontal gaze indicators HRGL, HRGP, HLGL, or HLGP, are 16 prism diopters or more, the photograph should not be used for the evaluation of photorefraction or pupillary light reflex (Bruckner test). Vertical gaze deviation of similar magnitude may also cause inaccuracy in these tests.

Another aspect of the present invention is the analysis of asymmetry between the right and left eyes of a subject. Large asymmetry between the sizes of the corneas can indicate developmental abnormality (e.g., microophthalmos or nanophthalmos) or enlargement of eye ball due to congenital glaucoma (e.g., buphthalmos). According to the present invention, asymmetry is preferably measured by the left/right ratio and left-right difference:

$$CDLRR = LCD/RCD$$

$$CDLRD = E*(LCD - RCD)$$

where CDLRR is the ratio between the left and right corneal diameters, CDLRD is the difference between the left and right corneal diameter, and E is a conversion factor. The conversion factor E converts apparent size in pixel count to absolute physical units, such as mm.

E=11.44 mm/CD if a calibration sticker is not used, where 11.44 mm is the average corneal diameter of an age-similar population.

E=19.05 mm/SD if a calibration sticker is used, where 19.05 mm is the diameter of the calibration sticker 18s (FIG. 10A).

Large asymmetry between the sizes of the pupils can indicate neurological abnormality (e.g. Horner's syndrome). According to the present invention, asymmetry is preferably measured by the left/right ratio:

$$PDLRR = LPD/RPD$$

$$PDLRD = E*(LPD - RPD)$$

where PDLRR is the ratio between the left and right pupil diameters, PDLRD is the difference between the left and right pupil diameter, and E is a conversion factor as defined above.

Large asymmetry between the color or brightness of the pupillary light reflex can indicate cataract, other opacities in the ocular media, retinoblastoma, or other intraocular mass. Referring to FIGS. 10A and 11, to evaluate the pupillary light reflexes it is necessary to first remove crescents 214 and corneal reflexes 216 from the pupillary circles 213 from both the right and left eyes 186L, 186R (removing meaning setting the color and brightness values of those pixels to null, undefined, or invalid). The remaining valid regions of the color maps and brightness maps of the left and right pupillary reflexes 142 are then subtracted to obtain color and brightness difference maps. The average and root-mean-square values of the difference maps are then used as indicators of asymmetry. Apparent asymmetry in pupillary reflex color or brightness could result from gaze deviation or spurious corneal reflections from extraneous external light sources. Therefore, the numerical indices are not definitive indicator of abnormality, but only alert flags for more sophisticated pattern analysis by computer or human expert.

The following summary report (Table 5) provides information on left-right eye asymmetry. Results outside 95% confidence interval are considered borderline and results outside 99% confidence intervals are considered outside of normal limits (abnormal).

TABLE 5

Left-Right Asymmetry Summary

| | Cornea Diameter | | Pupillary Light Reflex Diameter | | | | | |
|---|---|---|---|---|---|---|---|---|
| | L/R Ratio | L-R (mm) | L/R Ratio | L-R (mm) | Color | | Brightness | |
| | CDLRR | CDLRD | PDLRR | PDLRD | Avg | RMS | Avg | RMS |
| 95% CI | 0.97 to 1.06 | −0.4 to 0.6 | 0.88 to 1.10 | −0.7 to 0.5 | TBD | TBD | TBD | TBD |
| 99% CI | 0.96 to 1.07 | −0.5 to 0.8 | 0.84 to 1.14 | −0.9 to 0.7 | TBD | TBD | TBD | TBD |

CI: confidence interval from the clinical study.
TBD: to be determined in a clinical study.
Left-right difference in mm is calculated assuming corneal diameter of 11.44 mm (population average).

If the calibration sticker 182 (see FIG. 10A) is used, then the present invention also provides for the precise measurement of pupil diameters, corneal diameters and inter-corneal distance by multiplying the pixel count value by the conversion factor E as defined above.

Overall Operations of the System

Figure 15:
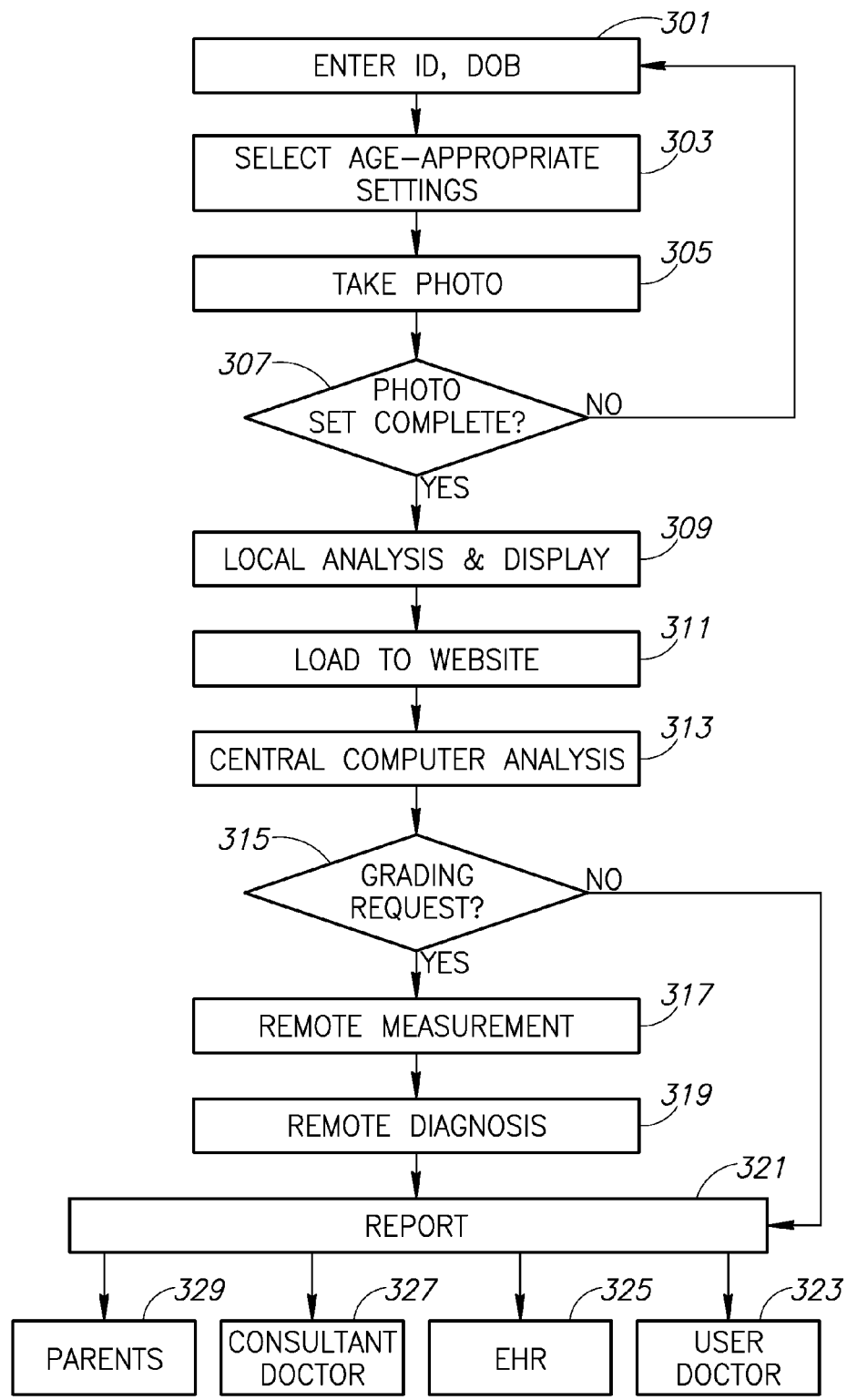
FIG. 15 is a diagram of a process for implementing the system shown in FIG. 1.

Referring to FIG. 15, in step 301 the operator 131 enters identifying (ID) information and date of birth (DOB) for the subject 132 (e.g., a child or infant) into the smart phone 120B (FIG. 1) prior to taking photographs. The smart phone application of the current invention then selects the appropriate set of photographic settings according to the patient's age (Tables 1, 2) in step 303. The operator 131 then takes a photograph in step 305. If the photograph is not satisfactory then it is discarded. If the photo is satisfactory, then the operator 131 adjusts the cropping and saves the cropped photograph. In step 307, the photography process is continued until the complete set (Tables 1, 2) of photographs is obtained as appropriate to the patient's age. In step 309, the photographs are then displayed on the display 124 of the smart phone 120B for the inspection by the operator and the user doctor (pediatrician, family practice doctor, optometrist or ophthalmologist) or parent. In one embodiment, the smart phone 120B also displays automated analysis (Tables 3-5) to provide a preliminary classification of the set of photographs as either within normal limits, borderline, or outside of normal limits.

The doctor or parent may choose to enter diagnostic impression at the time into the smart phone 120B or request grading by remote experts. The photographs, diagnostic impression, and requests are then uploaded to a website through the network 115 (FIG. 1) in step 311. In step 313 the central computer server 110 (FIG. 1) performs automated analysis (Tables 3-5). In step 315, if remote grading was requested then, steps 317 and 319 are performed. In step 317, an expert grading technician at a remote site makes adjustments to measurements and analyses using a remote client computer 120A and uploads this information to the server computer 110. In step 319, an expert grading doctor (e.g. pediatric ophthalmologist) reviews the measurement and analyses and provides definitive diagnostic impressions for upload to server computer 110.

In step 321a report is generated on the server computer 110 that includes patient ID, DOB, age, photographs, measurements and analyses (Table 3-5), and diagnostic impressions. The report is sent via the network 115 to the user doctor 323 and the electronic health record system (HER) 325 of the doctor's clinic or hospital. The user doctor can read the report either on the smart phone 120B or on a client computer 120A. The user doctor may also send a report to the parent 329 through the network 115. If the parents were the original user, the server computer 110 may send the report to the parents via the network 115. If a referral is made to a consultant doctor 327 (e.g. pediatric ophthalmologist or optometrist), then the user doctor or parent can send the report to the consultant doctor through the network 115.

One scenario for use of the system 100 is in the clinic of a general pediatrician performing a routine checkup of an infant or child. A technician takes the photographs as discussed above and shows the results to the pediatrician on the smart phone 120B. Alternatively, the photographs may be uploaded to the website and the pediatrician can view the report at the client computer 120A. The pediatrician then requests remote measurement and diagnosis. If the final report by the grading doctor shows abnormality, then the pediatrician refers the patient to a pediatric ophthalmologist and forwards the report via the network 115.

In another scenario, the parents are the users. A parent takes the photographs and views the results on the smart phone 120B. The parents then request remote measurement and diagnosis. If the final report by the grading doctor shows abnormality then the parents send the report to a pediatric ophthalmologist and requests an appoint for the patient. The website provides a list of local pediatric ophthalmologists and optometrists (with contact information and forwarding links) to facilitate the scheduling and report forwarding process.

Further, in some embodiments, the website includes a teaching section and examples of normal and abnormal red reflex digital images that parents or pediatricians can compare with images they have taken and learn how to optimize the detection and capture of a clinically-informative red reflex image.

Further, in some embodiments, the network 115 of mobile devices and servers in this invention is used to aggregate data from multiple clinics to assemble a large normative dataset (e.g., to define what is normal, borderline, and abnormal), to measure the incidence of various pediatric eye diseases, and to obtain the characteristic pattern of variables for each pediatric eye disease.

Computing Device

Figure 16:
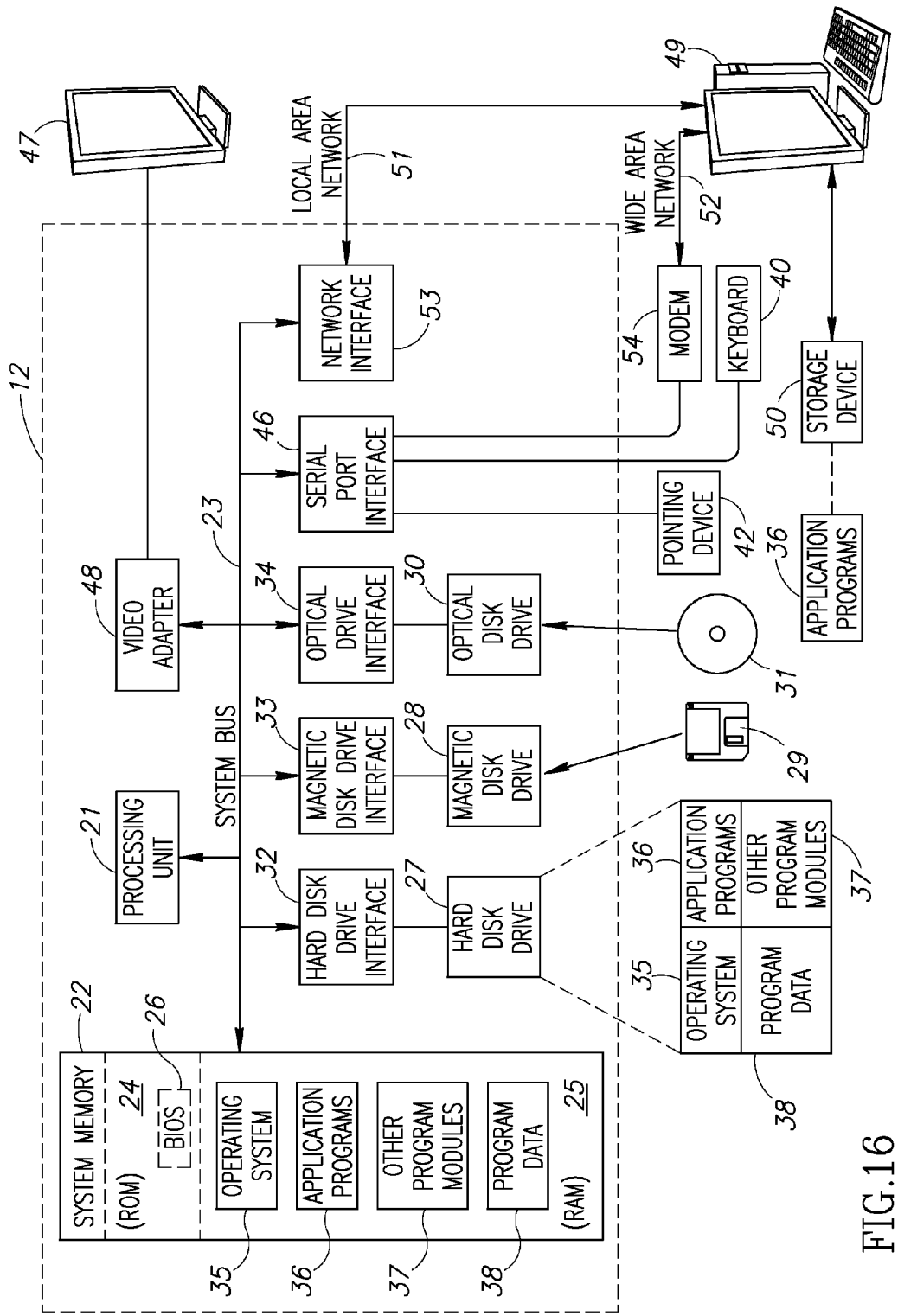
FIG. 16 is a diagram of a hardware environment and an operating environment in which the computing devices of the system of FIG. 1 may be implemented.

FIG. 16 is a diagram of hardware and an operating environment in conjunction with which implementations of the server 110 and the computing devices 120A-C may be practiced. The description of FIG. 16 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 16 includes a general-purpose computing device in the form of a computing device 12. The server and the computing devices 120A-C may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard 5 disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as solid state memory devices ("SSD"), magnetic cassettes, flash memory cards, USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, motion detection/recognition device (e.g. Microsoft Kinect® system), or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feedback game controller).

The computing device 12 may operate in a networked environment using logical connections to one or more remote computers, such as remote computer 49. These logical connections are achieved by a communication device coupled to or a part of the computing device 12 (as the local computer) Implementations are not limited to a particular type of communications device.

The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 16 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN networking environment, the computing device 12 typically includes a modem 54, a type of communications device, or any other type of communications device for establishing communications over the wide area network 52, such as the Internet.

The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

Although the eccentric photorefraction, Hirschberg, and Bruckner tests are all established tests that have been previously used, there had not been a way to perform these tests within the limited capabilities of the smart phone camera and flash. These are provided for in the present invention.

First, eccentric photorefraction on the typical smart phone is ideally carried out at a relatively close working distance due to the wide angle nature of the camera lens and the close distance between the flash and the camera lens. Thus, a means is needed to establish working distance. There is no special range finding device on the typical smart phone, unlike a specialized photorefraction instrument such as the PlusOptix® systems. According to the present invention, this difficulty is circumvented by the use of an outline mask overlay on the smart phone screen. The mask contains outlines of eyes so that the inter-eye distance can be matched with the outline. In the clinical study, the inter-eye distance (measured between the centers of the corneas as defined by limbal circles) was 50.7 mm with a population coefficient of variation of 5% in a group of 65 children aged 3.4 to 5.3 years. Thus, by using the mask method carefully, the working distance could be established to a good level of accuracy. The present invention also established the ideal setting of working distance as approximately 47 cm, corresponding to a flash-camera lens distance of 0.7 degrees in visual angle. Variation around this value would also work and this invention is not limited by the exact value of the working distance.

Further, the present invention allows for the orientation of the flash relative to the camera lens to be varied by varying the orientation of the mask, allowing for measurement of photorefraction in at least 2 orthogonal axes to measure astigmatism. Traditionally, photorefraction was measured from the width (e.g., in mm) of the crescent. The present invention improves the method by using the crescent width to pupil diameter ratio (CPR). This partially reduces the photorefraction error due to working distance variation and pupil size. Furthermore, the present invention teaches the use of a sigmoidal curve fit, preferably with a logit function, to convert CPR to an estimated photorefraction value in diopters.

The present invention also allows for the use of an eccentric small flash by setting the working distance such that a crescent reflection is unlikely to interfere with the Hirschberg test. This distance was found to be approximately 30 cm, corresponding a flash-camera lens distance of 1.1 degrees in visual angle. Variation around this value would also work and this invention is not limited by the exact value of the working distance. Traditionally, the photographic Hirschberg test uses the displacement (e.g., in mm) of the corneal reflex from the pupillary axis (pupil-corneal reflex offset) to estimate strabismus in terms of prism diopters. The present invention teaches the use of the ratio between the pupil-corneal reflex offset and corneal diameter to estimate strabismus angle. This reduces error that could arise from variation in working distance and thereby image magnification. It also reduces error from variation in corneal curvature, which is related to corneal diameter.

Further, the Bruckner test is traditionally done with coaxial illumination with a beam that illuminates a broad area of the retina. The present invention allows for the use of an eccentric small flash by setting the working distance such that a crescent reflection is unlikely to interfere. This distance was found to be approximately 30 cm, corresponding a flash-camera lens distance of 1.1 degrees in visual angle. Variation around this value would also work and this invention is not limited by the exact value of the working distance. Further, the present invention allows for the orientation of the flash relative to the camera lens to be varied by varying the orientation of the outline mask, allowing for illuminating at least two retinal locations to increase the chance of detecting retinoblastoma or other intraocular mass. Traditionally, the Bruckner test relies on visual inspection only. The present invention also teaches the use of quantitative analysis of the left-right asymmetry in pupillary light reflex color and brightness as an aid in detecting abnormality.

This invention also teaches the use of the corneal diameter or a sticker diameter as calibration metrics to estimate the physical dimensions (e.g., in mm) of eye anatomy (diameters, distances, and their left-right differences). This reduces error due to variation in working distance and thereby image magnification.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A handheld computing device for providing a screening test for a subject's left eye and right eye, the computing device comprising:
    an image capturing device;
    a light generating device;
    a display;
    a data storage comprising an image capturing application including programming data configured to display a mask comprising a left eye frame and a right eye frame on the display, the mask having a mask orientation configured to facilitate positioning the computing device to align, on the display, the left eye frame and the right eye frame of the mask with the left eye and the right eye of the subject, respectively, and the mask having a desired distance spacing the left eye frame and the right eye frame apart from each other, the desired distance configured to facilitate positioning the light generating device at a working distance from the left eye and the right eye by simultaneously positioning, on the display, a selected portion of the left eye within the left eye frame of the mask and a selected portion of the right eye within the right eye frame of the mask to align an inter-eye distance of the subject with the desired distance between the left eye frame and the right eye frame; and
    a processor operatively coupled to the image capturing device, the light generating device, and the display, the processor being operative to execute the image capturing application to perform an eye test by:
        displaying the mask overlaying a current image of the image capturing device on the display;
        operating the light generating device to illuminate the subject's eyes;
        capturing an image containing both the left eye and right eye at the working distance when the subject's eyes are illuminated, the computing device is positioned to align the left eye frame and the right eye frame of the mask with the left eye and the right eye of the subject, respectively, at the mask orientation, and the inter-eye distance is aligned with the desired distance in the mask using the image capturing device;
        displaying the captured image on the display for inspection by the operator;
        analyzing the captured image to provide information regarding the presence or absence of an eye condition; and
        displaying the results of the analysis on the display of the computing device.

2. The computing device of claim 1, wherein the eye test comprises an eccentric photorefraction test, a corneal light reflex test, and a pupillary light reflex test.

3. The computing device of claim 1, further comprising a visual attractor coupled to the computing device at a location proximate to the image capturing device.

4. The computing device of claim 1, wherein the image capturing application is configured to display a first outline mask during performance of a first eye test and a second outline mask during performance of a second eye test, the second outline mask larger than the first outline mask so that the working distance is greater for the first eye test than for the second eye test.

5. The computing device of claim 1, wherein analyzing the captured image comprises determining a preliminary classification of the captured image as within normal limits, borderline, or outside of normal limits for one or more criteria.

6. The computing device of claim 1, wherein the computing device further includes a communication device operative to facilitate communication with other computing devices over a network, and the image capturing application is operative to send the captured image to a different computing device over the network.

7. The computing device of claim 1, wherein the computing device comprises a smart phone or a tablet computer.

8. The computing device of claim 1, wherein the image capturing device is offset from the light generating device by a distance, and the image capturing application is operative to instruct the operator to capture, using the image capturing device, a first image at a first orientation relative to the light generating device and a second image at a second orientation relative to the light generating device different than the first orientation to facilitate measurement of photorefraction in different axes by displaying a first outline mask at a first orientation relative to the computing device and a second outline mask at a second orientation relative to the computing device so that the operator is instructed to rotate the computing device relative to the subject to capture images at different orientations.

9. The computing device of claim 1, wherein the image capturing application is configured to cause the display to display one of a plurality of differently sized masks on the display when the operator is capturing the image, the size of the one mask displayed being dependent on a desired working distance of the light generating device to the left eye and the right eye of the subject.

10. The computing device of claim 9, wherein each of the plurality of masks includes the left eye frame and the right eye frame that corresponds to the subject's eyes.

11. The computing device of claim 9, wherein the image capturing device is offset from the light generating device by an offset distance, and the size of the displayed mask is selected to establish the working distance for the eye test such that the offset distance corresponds to a viewing angle that helps prevent a crescent reflection from interfering with a corneal light reflex test measurement.

12. The computing device of claim 1, wherein the image capturing application is operative to utilize the size of an object in the captured image to estimate physical dimensions of eye anatomy of the subject.

13. The computing device of claim 12, wherein the object comprises a cornea of the subject or a calibration sticker.

14. The computing device of claim 1, wherein the eye test comprises an eccentric photorefraction test with the processor being operative to execute the image capturing application to perform the eccentric photorefraction eye test by:
   operating the light generating device to illuminate the subject's eyes;
   capturing an image of a first pupil of a first eye and a second pupil of a second eye using the image capturing device;
   measuring a width of a first crescent of the first pupil appearing in the image;
   obtaining a diameter of the first pupil;
   determining a ratio of the width of the first crescent to the diameter of the first pupil to define a crescent width to pupil diameter ratio (CPR) for the first eye; and
   utilizing the CPR for the first eye as a measurement tool for the eccentric photorefraction eye test.

15. The computing device of claim 14, wherein the image capturing application is further operative to:
   measure a width of a second crescent of the second pupil appearing in the image;
   obtain a diameter of the second pupil;
   determine a ratio of the width of the second crescent to the diameter of the second pupil to define a crescent width to pupil diameter ratio (CPR) for the second eye; and
   compare the CPR for the first eye to the CPR for the second eye to detect anisometropia.

16. The computing device of claim 14, wherein the image capturing application is further operative to: convert the first CPR to an estimate of photorefraction using a non-linear function.

17. The computing device of claim 16, wherein the non-linear function is a logit function.

18. The computing device of claim 16, wherein the non-linear function is a sigmoidal function.

19. The computing device of claim 1, wherein the processor is further operative to execute the image capturing application to:
   display left guidelines and right guidelines on the display; and
   adjust the position of the captured image on the display to position (i) a left eye pupil between the left guidelines displayed on the display, and (ii) a right eye pupil between the right guidelines displayed on the display.

20. The computing device of claim 1, wherein the left eye outline is an elliptical outline configured to be positioned around a visible scleral region of the left eye, and the right eye outline is an elliptical outline configured to be positioned around a visible scleral region of the right eye.

21. The computing device of claim 1, the image capturing application including programming data for displaying one of a plurality of masks each comprising a left eye frame and a right eye frame spaced apart by a desired distance, the plurality of masks each having a different desired distance, and the processor executing the image capturing application being further operative to perform the eye test by:
   selecting, before displaying selected mask on the display, one of the plurality of masks having a desired distance corresponding to the working distance; and
   positioning the light generating device at the working distance from the left eye and the right eye by simultaneously positioning, on the display, the selected portion of the left eye within the left eye frame of the selected mask and the selected portion of the right eye within the right eye frame of the selected mask to align the inter-eye distance of the subject with the desired distance between the left eye frame and the right eye frame.

22. The computing device of claim 1, wherein the eye test comprises an eccentric photorefraction test with the processor being operative to execute the image capturing application to perform the eccentric photorefraction eye test by:
   displaying a first outline mask on the display that allows an operator to align the subject with the first outline mask to ensure a first image is captured at a horizontal orientation;
   operating the light generating device to illuminate the subject's eyes;
   capturing the first image of a first pupil of a first eye and a second pupil of a second eye in the horizontal orientation using the image capturing device;
   displaying a second outline mask on the display that allows the operator to align the subject with the second outline mask to ensure a second image is captured at a vertical orientation;
   operating the light generating device to illuminate the subject's eyes;
   capturing the second image of the first pupil and the second pupil in the vertical orientation using the image capturing device;
   using the first image, measuring the widths of a horizontal crescent of each of the first pupil and the second pupil;
   using the second image, measuring the widths of a vertical crescent of each of the first pupil and the second pupil;
   obtaining a diameter of the first and second pupil;
   for each of the first and second eyes, determining a ratio of the width of the horizontal crescent to the diameter of the pupil to define a horizontal crescent width to pupil diameter ratio (CPR); for each of the first and second eyes, determining a ratio of the width of the vertical crescent to the diameter of the pupil to define a vertical crescent width to pupil diameter ratio (CPR); and utilizing the horizontal CPR and the vertical CPR for each of the first and second eyes to evaluate cardinal astigmatism.

23. The computing device of claim 22, wherein utilizing the horizontal CPR and the vertical CPR for each of the first and second eyes to evaluate cardinal astigmatism comprises converting the horizontal CPR and the vertical CPR to an estimate of photorefraction using a non-linear function.

24. A handheld computing device for providing a screening test for a subject's left eye and right eye, the computing device comprising:

an image capturing device;

a light generating device;

a display;

a data storage comprising an image capturing application including programming data for displaying one of a plurality of masks each comprising a left eye frame and a right eye frame on the display, the plurality of masks each having a mask orientation configured to facilitate positioning the computing device to align, on the display, the left eye frame and the right eye frame of each mask with the left eye and the right eye of the subject, respectively, and each mask having a desired distance spacing the left eye frame and the right eye frame apart from each other, the desired distance configured to facilitate positioning the light generating device at a working distance from the left eye and the right eye by simultaneously positioning, on the display, a selected portion of the left eye within the left eye frame of the mask and a selected portion of the right eye within the right eye frame of the mask to align an inter-eye distance of the subject with the desired distance between the left eye frame and the right eye frame, the plurality of masks each having a different desired distance; and a processor operatively coupled to the image capturing device, the light generating device, and the display, the processor being operative to execute the image capturing application to perform an eye test by:

selecting one of the plurality of masks having a size corresponding to a desired working distance;

displaying the selected mask overlaying a current image of the image capturing device on the display;

positioning the computing device according to a mask orientation aligning, on the display, the left eye frame and the right eye frame of the selected mask with the left eye and the right eye of the subject;

positioning the computing device at the desired working distance from the left eye and the right eye by simultaneously positioning, on the display, a selected portion of the left eye within the left eye frame of the selected mask and a selected portion of the right eye within the right eye frame of the selected mask to align an inter-eye distance of the subject with the desired distance between the left eye frame and the right eye frame;

operating the light generating device to illuminate the subject's eyes;

capturing an image containing both the left eye and right eye at the desired working distance when the subject's eyes are illuminated, the computing device is positioned to align the left eye frame and the right eye frame of the mask with the left eye and the right eye of the subject, respectively, at the mask orientation, and the inter-eye distance is aligned with the desired distance in the selected mask using the image capturing device;

displaying the captured image on the display for inspection by the operator;

analyzing the captured image to provide information regarding the presence or absence of an eye condition; and displaying the results of the analysis on the display of the computing device.

* * * * *